(12) United States Patent
Koerber et al.

(10) Patent No.: US 11,648,369 B2
(45) Date of Patent: May 16, 2023

(54) HUMIDIFICATION OF A PRESSURIZED FLOW OF BREATHABLE GAS

(71) Applicant: KONINKLIJKE PHILIPS N.V., Eindhoven (NL)

(72) Inventors: Achim Gerhard Rolf Koerber, Eindhoven (NL); Rainer Hilbig, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 707 days.

(21) Appl. No.: 16/468,698

(22) PCT Filed: Dec. 14, 2017

(86) PCT No.: PCT/EP2017/082848
§ 371 (c)(1),
(2) Date: Jun. 12, 2019

(87) PCT Pub. No.: WO2018/109095
PCT Pub. Date: Jun. 21, 2018

(65) Prior Publication Data
US 2019/0314598 A1    Oct. 17, 2019

Related U.S. Application Data

(60) Provisional application No. 62/433,875, filed on Dec. 14, 2016.

(51) Int. Cl.
*A61M 16/16* (2006.01)
*A61M 16/10* (2006.01)
*A61M 16/20* (2006.01)
*A61M 11/00* (2006.01)
(Continued)

(52) U.S. Cl.
CPC ........ *A61M 16/161* (2014.02); *A61M 11/005* (2013.01); *A61M 16/108* (2014.02);
(Continued)

(58) Field of Classification Search
CPC ... A61M 16/108; A61M 16/16; A61M 16/161
See application file for complete search history.

(56) References Cited

U.S. PATENT DOCUMENTS 5,031,612 A     7/1991  Clementi
5,148,801 A *   9/1992  Douwens .......... A61M 15/0015
                                                128/203.29
(Continued)

FOREIGN PATENT DOCUMENTS

DE      3707228 A1      9/1987
WO      2011058371 A1   5/2011

*Primary Examiner* — Margaret M Luarca
(74) *Attorney, Agent, or Firm* — Daniel H. Brean; Andrew M. Gabriel

(57) ABSTRACT

A system (10) configured to facilitate humidification of a pressurized flow of breathable gas delivered to a subject (12) comprises a pressure generator (14), a nebulizer (16), a heater (38), one or more hardware processors (22), and/or other components. The pressure generator is configured to generate a pressurized flow of breathable gas for delivery to an airway (24) within a trachea of the subject. The nebulizer is configured to provide fluid droplets (54) to the breathable gas. The heater is configured to heat a volume of the breathable gas before the droplets are supplied to the breathable gas. The breathable gas received by the subject exhibits a target temperature and humidity level at short distance d from the nebulizer due to one or more of a number of the droplets, an average size of the droplets, a gas flow rate, and/or an amount of heating power.

18 Claims, 6 Drawing Sheets

Figure 1:
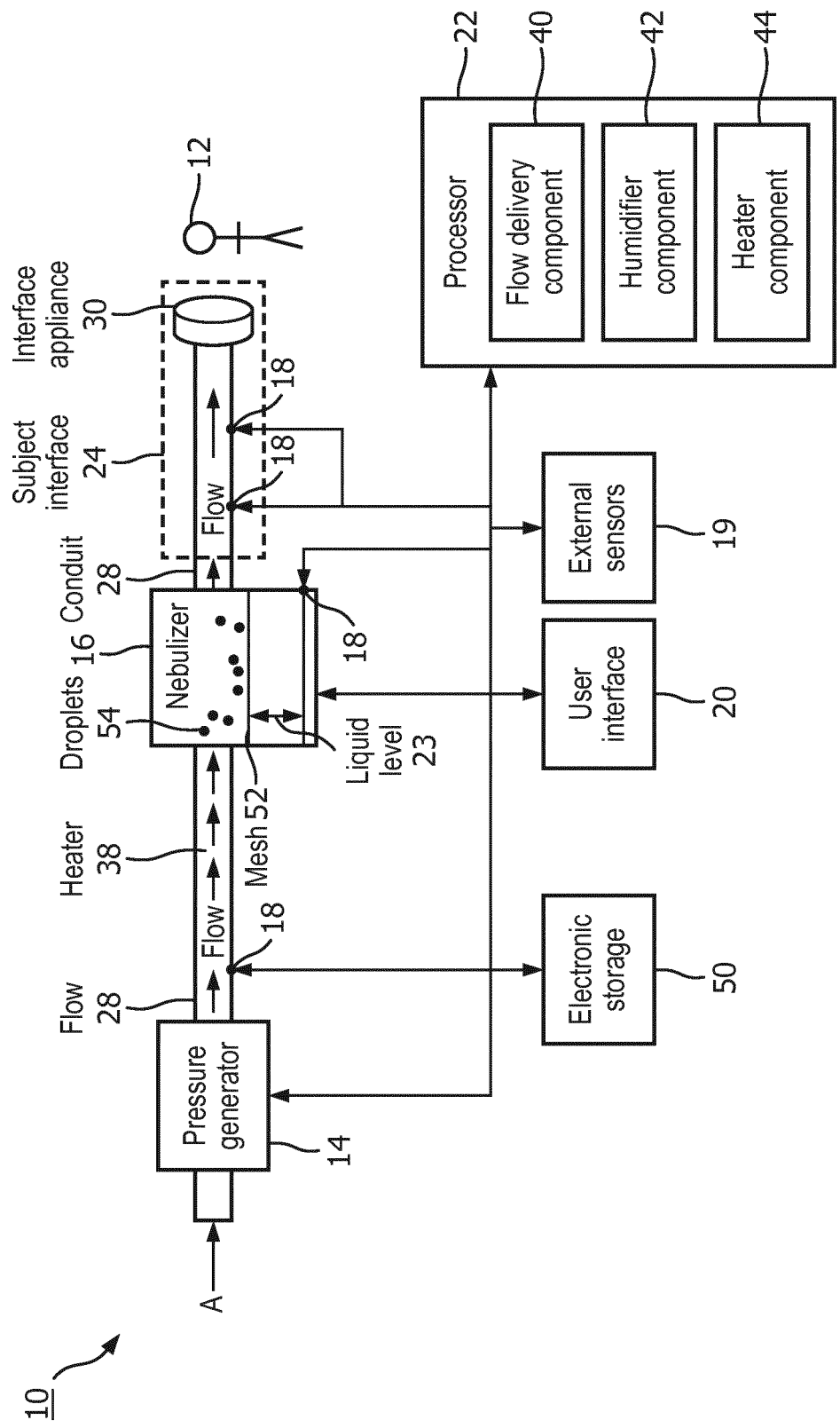

(51) Int. Cl.
*A61M 16/00* (2006.01)
*A61M 16/04* (2006.01)

(52) U.S. Cl.
CPC ....... *A61M 16/204* (2014.02); *A61M 16/0069* (2014.02); *A61M 16/0465* (2013.01); *A61M 2016/0024* (2013.01); *A61M 2016/0027* (2013.01); *A61M 2016/0036* (2013.01); *A61M 2205/3368* (2013.01); *A61M 2205/3553* (2013.01); *A61M 2205/505* (2013.01); *A61M 2205/52* (2013.01)

(56) References Cited

U.S. PATENT DOCUMENTS

| | | |
|---|---|---|
| 8,056,558 B2 | 11/2011 | Bracken |
| 9,119,933 B2 | 9/2015 | Bedford et al. |
| 9,289,570 B2 | 3/2016 | Rik et al. |
| 9,308,333 B2 | 4/2016 | Minocchieri et al. |
| 9,375,548 B2 | 6/2016 | Mabini et al. |
| 2003/0033055 A1* | 2/2003 | McRae ................. B05B 9/002 700/282 |
| 2008/0149100 A1 | 6/2008 | Van Holst et al. |
| 2015/0007817 A1* | 1/2015 | Longest ............ A61M 16/1095 128/203.14 |
| 2015/0250969 A1* | 9/2015 | Xavier .................. A61B 46/00 128/200.26 |
| 2015/0367089 A1* | 12/2015 | Arimoto ................. C25D 5/02 205/112 |
| 2017/0216552 A1* | 8/2017 | Goff ................. A61M 16/0816 |
| 2017/0266408 A1 | 9/2017 | Giovannelli et al. |
| 2018/0250490 A1 | 9/2018 | Burgess et al. |

\* cited by examiner

HUMIDIFICATION OF A PRESSURIZED FLOW OF BREATHABLE GAS

CROSS-REFERENCE TO PRIOR APPLICATIONS

This application claims the priority benefit under 35 U.S.C. § 371 of International Patent Application No. PCT/EP2017/082848, filed on Dec. 14, 2017, which claims the priority benefit of U.S. Provisional Patent Application No. 62/433,875, filed on Dec. 14, 2016, the contents of which are herein incorporated by reference.

BACKGROUND OF THE INVENTION

1. Field of the Invention

The present disclosure pertains to systems and methods for facilitating humidification of a pressurized flow of breathable gas delivered to a subject.

2. Description of the Related Art

It is well known to ventilate a subject's (e.g., a patient's) airway to supply a pressurized flow of breathable gas to the subject. Humidification technologies for ventilation have been developed. One kind of humidification device is a so-called "heated humidifier" where the flow of breathable gas is conducted over a heated water reservoir. In the application of humidification of air for ventilated subjects (e.g., patients), these devices are targeted to deliver an air flow of at least 33° C. temperature at a relative humidity close to 100%. The disadvantage of these devices is the high heating power (~60-70 W) needed to heat the water reservoir and to evaporate the water vapor. Furthermore, they are bulky and pose a security risk, since they might be a source of thermal injury to human skin.

So-called "personal humidifiers" are devices within the air supply from a ventilator (e.g., a pressure generator) that are located close to the tracheal cannula of the subject. These devices have the advantage that they are light-weight and have low power consumption (~3-5 W). These nebulizers may inject droplets having, for example, ~5 µm diameters at a target rate of ~33 mg/L into the air stream during inhalation to raise the humidity of the air delivered to the subject. One example of a nebulizer head for use in a "personal humidifier" would be a "vibrating mesh nebulizer" manufactured by Aerogen, Inc.

When water or saline droplets of ~5 µm diameter are injected into the inhaled air at a rate of ~33 mg/L, the temperature of the mist will drop due to partial evaporation of the droplets. Due to fast energy exchange with the air molecules, the air/droplet mist entering the subject's airways will have a temperature several degrees Celsius below the original temperature of the air but at a relative humidity of 100%. Such a comparatively cold and therefore dry air inflow (100% relative humidity (RH) at the lower temperature corresponds to a lower absolute water vapor concentration than 100% RH at room temperature) may induce a marked heat and water vapor flow from the skin of the subject's upper trachea into the inhaled airflow. The skin of the subject's upper trachea may thus be cooled and dried out which will lead to an uncomfortable feeling and an increased risk of infection and ciliary dysfunctionality. The droplets might be not able to prevent the drying out of the tracheal skin, because only a small fraction (e.g. 10-30%) of the droplets will be deposited at the trachea surface.

As an example, consider a scenario with an air inflow of 30 liters per minute (LPM) with an air temperature ($T_{air}$) equal to 20° C. with 64% relative humidity.) When water or saline droplets of ~5 µm diameter are injected into the inhaled air at a rate of ~33 mg/L, the temperature of this mist will drop within ~5 ms by ~4.4° C. due to partial evaporation of the droplets. If the air stream from the ventilator has a temperature of 20° C. and a water vapor concentration of 11 mg/L (which equals 64% relative humidity), then the air/droplet mist entering the patient's airways will thus have a temperature of 15.6° C. at a relative humidity of 100% (i.e., a water vapor concentration of 13.4 mg/L).

Furthermore, a large fraction (up to 90%) of the droplets of ∥5 µm diameter will be lost from the air stream by collision with the walls of the bend of the tracheal cannula. This mechanism is known in the literature as "impaction." Impaction will lead to a liquid film covering the lower surface of the tracheal cannula, and gravity will help to form large (~1 mm diameter) droplets of liquid at the lower rim of the cannula from which those large droplets may drop into the trachea and the lower airways (e.g., bronchi and bronchioles). Also this effect might lead to an uncomfortable feeling and an increased risk of infection.

Therefore, a device is missing in the art that combines the advantages of a "personal humidifier" (light-weight, low power) and an adequate temperature and humidity level at the subject interface without the need of high power consumption, which would make a mobile application impossible (e.g., for a patient in a wheelchair).

SUMMARY OF THE INVENTION

Accordingly, one or more aspects of the present disclosure relate to a system configured to facilitate humidification of a pressurized flow of breathable gas delivered to a subject. The system comprises a pressure generator, a nebulizer, a heater, one or more hardware processors, and/or other components. The pressure generator is configured to generate a pressurized flow of breathable gas for delivery to an airway within a trachea of the subject. The nebulizer is configured to provide fluid droplets to the breathable gas. The heater is configured to cause the pressure generator to deliver a flow of breathable gas to the subject; cause the nebulizer to provide fluid droplets to the breathable gas; and cause the heater to heat a volume of the breathable gas before fluid droplets are supplied to the breathable gas. The breathable gas received by the subject exhibits a target temperature and humidity level at short distance d from the nebulizer due to one or more of a number of the droplets, an average size of the droplets, a gas flow rate, and/or an amount of heating power.

Yet another aspect of the present disclosure relates to a method for facilitating humidification of a pressurized flow of breathable gas delivered to a subject with a system. The system comprises a pressure generator, a nebulizer, a heater, and one or more hardware processors. The method comprises generating, with the pressure generator, a pressurized flow of breathable gas for delivery to an airway within a trachea of the subject; providing fluid droplets, with the nebulizer, to the pressurized flow of breathable gas; and heating, with the heater, a volume of the breathable gas before moisture is supplied to the breathable gas. The breathable gas received by the subject exhibits a target temperature and humidity level at short distance d from the nebulizer due to one or more of a number of the droplets, an average size of the droplets, a gas flow rate, and/or an amount of heating power.

Still another aspect of the present disclosure relates to a system for facilitating humidification of a pressurized flow of breathable gas delivered to a subject. The system comprises means for generating a pressurized flow of breathable gas for delivery to an airway within a trachea of the subject; means for providing fluid droplets to the pressurized flow of breathable gas; and means for heating a volume of the breathable gas before moisture is supplied to the breathable gas. The breathable gas received by the subject exhibits a target temperature and humidity level at short distance d from the means for providing fluid droplets due to one or more of a number of the droplets, an average size of the droplets, a gas flow rate, and/or an amount of heating power.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 1 illustrates a system configured to facilitate humidification of a pressurized flow of breathable gas delivered to a subject, in accordance with one or more embodiments;

FIG. 2 illustrates a view of a graphical user interface presented to the subject, in accordance with one or more embodiments;

FIG. 3 illustrates a second view of the graphical user interface, in accordance with one or more embodiments;

FIG. 4 illustrates a system configured to facilitate humidification of a pressurized flow of breathable gas delivered to a subject, in accordance with one or more embodiments;

FIG. 5 illustrates a simulation model of a personal nebulizer, in accordance with one or more embodiments;

FIG. 6 illustrates a simulation model of a personal nebulizer, in accordance with one or more embodiments;

FIG. 7 illustrates a simulation model of a personal nebulizer, in accordance with one or more embodiments; and FIG. 8 illustrates a method for facilitating the addition of droplets to a pressurized flow of breathable gas delivered to a subject, in accordance with one or more embodiments.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to facilitate humidification of a pressurized flow of breathable gas delivered to a subject 12. In some embodiments, the present technology can be applied as an optimized "personal humidifier" for (ventilated) subjects breathing via a tracheostoma. In some embodiments, system 10 includes one or more of a pressure generator 14, a nebulizer 16, a subject interface 24, a sensor(s) 18, a user interface 20, a processor 22, electronic storage 50, and/or other components. A fast air heater, such as heater 38 of FIG. 4, may also be provided. In some embodiments, heater 38 may be located between pressure generator 14 and a droplet injector, such as nebulizer 16. Heater 38 may also be located in apposition with nebulizer 16, in some embodiments. In some embodiments, a fast temperature sensor, such as a sensor 18, may be located at an entrance to a subject (such as a conduit 28) of the tracheal cannula, a mask, etc.

In some embodiments, a personal nebulizer may include one or more of the tracheal cannula, conduit 28, subject interface 24, interface appliance 30, and/or other elements. In some embodiments, heater 38 may be within conduit 28. In other embodiments, conduit 28 may pass through heater 38. In some embodiments, a time-dependent air heating power is modulated and proportional to a flow of air (flow of breathable gas), wherein there is no heating during exhalation. In some embodiments, heater 38 includes a fast heating element with a time constant of less than 1 second to maintain the temperature of the flow of breathable gas constant during inhalation (because gas flow varies during inhalation) and to ensure safety (i.e., a fast switch-off is made if nebulizer 16 is failing. All other suitable time constants are contemplated.

System 10 is configured to provide a humidity- and temperature-controlled pressurized flow of breathable gas to subject 12. In some embodiments, instead of cold room air, a supply warm air is provided to nebulizer 16, which is generating a mist of water. The air flow for inspiration coming from the ventilator, such as pressure generator 14, is passed through heater 38 where a time-dependent heating power P(t) is transferred to the breathing gas. The final gas/mist mixture temperature, needed heating power, and also needed minimum distance of the nebulizer to the "trach" are determined by the gas flow rate, water droplet amount and size, and start gas temperature. In some embodiments, as discussed herein, this minimum distance ranges from about 1 cm to about 30 cm. Advantageously, the mixture will have 100% relative humidity in some embodiments.

This air temperature and humidity (close to the situation found when using a "conventional" vapor humidifier, which is based on saturating the inhaled air with water vapor above a heated water reservoir) causes less heat and water vapor loss from the subject's upper trachea with respect to previous droplet nebulizers.

In some embodiments, after establishing this air/droplet mist equilibrium, droplets 54 are partially evaporated and thus have a reduced diameter. Advantageously, those droplets 54 (with reduced diameters) have a much higher probability of reaching the airways of subject 12 without hitting the walls of the tracheal cannula bend. Input parameters can also be chosen to influence and/or optimize the size of droplets 54 remaining in the air/droplet mist mixture. That is, the droplet size is adapted to the geometry of the used "trach tube," for example.

More specifically, in some embodiments, instead of cold room air a supply warm air of ~48° C. is provide to nebulizer 16 (the "personal humidifier"), which is generating a mist of water droplets of ~5 μm diameter at a rate of ~16 mg/L (e.g., at about half the target rate of a prior droplet nebulizer). Numerical simulations show that the equilibrium composition of the air/droplet mist entering subject's 12 airways will then have a temperature of 25° C. at a relative humidity of 100% (corresponding to a water vapor concentration of 23.4 mg/L) and that this equilibrium will be reached within short time (~10 ms) or, correspondingly, within a short distance (less than 7.5 cm when taking the maximum gas velocity on the axis during inhalation as 7.5 m/s). This air temperature and humidity (close to the situation found when using a "conventional" vapor humidifier which is based on saturating the inhaled air with water vapor above a heated water reservoir) causes less heat and water vapor loss from subject's 12 upper trachea with respect to the prior droplet nebulizers.

In some embodiments, a "trach tube," or tracheal cannula (conduit 28) has an inner diameter of 8 mm and a curvature radius of 20 mm. However, all other inner diameters and curvature radii are contemplated. After establishing the air/droplet mist equilibrium, the droplets are partially evaporated and thus have a reduced diameter (reduced from 5 μm to 3 μm) because the mass rate output of the nebulizer is reduced in some embodiments (from 33 mg/L to 16 mg/L). At 33 mg/L droplets 54 would have a diameter of 4.3 μm after establishing equilibrium. As mentioned, those droplets 54 having a reduced diameter (reduced from 5 μm to 3 μm) have a much higher probability of reaching the airways without hitting the walls of the tracheal cannula bend. (Assuming a peak volume flow of 70 L/min during inhalation it is simulated that 62% of the 5 μm diameter droplets would hit the trach walls, whereas this number would be only 10% for the 3 μm diameter droplets). If considerably fewer droplets are hitting the tracheal cannula's walls, then the risk of forming large drops of water at the lower rim of the trach that would drop into the lower airways is greatly reduced.

In some embodiments, the air flow for inspiration coming from pressure generator 14 is passed through heater 38 where a time-dependent heating power P(t) is transferred to the breathable gas. Ideally, the heating power P(t) should be proportional to the gas flow Φ(t). To reach the desired temperature of 48° C., a heating energy density of about 36 J/L is required. Assuming a tidal volume of 0.5 L and a duration of 1 s for the inspiration phase, an average heating power of 36 J/L*0.5 L/1 s=18 W can be estimated.

As mentioned herein, for security and/or safety reasons, a fast temperature sensor at the entrance of the tracheal cannula (or other entrance to the subject) is added to trigger switch-off of the air heater if the nebulizer fails to produce droplets. The mass rate of the nebulizer is adjusted (i.e., reduced) from ~33 mg/L to ~16 mg/L so that droplet 54 diameter is reduced (from 5 μm to 3 μm) during the equilibration phase. It should be noted that the numbers mentioned within this disclosure are merely exemplary and not intended to be limiting. All other suitable numbers and values are contemplated to be used with the present technology in various embodiments.

In some embodiments, system 10 is configured to provide a humidity controlled pressurized flow of breathable gas to subject 12 according to a predetermined pressure support therapy regime. System 10 is configured to generate output signals and/or determine various parameters related to the pressurized flow of breathable gas. System 10 is configured to receive feedback from subject 12 related to a comfort level of subject 12 during therapy. System 10 is configured to automatically adjust the pressurized flow of breathable gas and/or the predetermined therapy regime, provide feedback to subject 12, and/or prompt subject 12 to make manual adjustments based on the output signals, the determined parameters, the feedback from subject 12, and/or other information. The feedback provided to subject 12 may include, for example, a recommendation to try a different therapy regime and/or alternate therapy devices, and/or other feedback. The manual adjustments may be, for example, manual adjustments to one or more components of system 10, manual adjustments to the ambient environment, and/or other manual adjustments. System 10 is configured to simplify adjustments to humidity control and/or pressure support therapy that enhance the comfort level of subject 12 during therapy.

For example, system 10 may determine, obtain, and/or receive information related to an ambient temperature, a relative ambient humidity, leak, the humidification method, humidification method set points (e.g., a target humidity level, etc.), a subject interface (e.g., conduit) temperature, water usage (e.g., per hour and/or per session), and/or other parameters. System 10 may receive feedback from subject 12 that includes information related to an inhaled air temperature rating (e.g., 0 being too cold, 10 being too hot), an inhaled air moisture rating (e.g., 0 being too dry, 10 being too wet), whether or not subject 12 has experienced tube rainout, whether or not subject 12 has experienced mask rainout, and/or other information. System 10 is configured to analyze the parameter information and the feedback from subject 12 and make an automatic adjustment to the pressure support therapy regime, provide feedback to subject 12, prompt subject 12 and/or other users to make a manual adjustment to system 10 and/or the ambient environment, and/or take other actions. Other users may include a doctor, a caregiver, and/or other users. System 10 reduces the burden on subject 12 to determine which adjustments to make to increase his comfort level during therapy.

As illustrated in FIG. 1, pressure generator 14 is configured to generate a pressurized flow of breathable gas for delivery to an airway of subject 12. Pressure generator 14 is also configured to facilitate humidification of the pressurized flow of breathable gas delivered to subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the flow rate and/or pressure of the flow of gas to provide pressure support to the airway of subject 12.

Pressure generator 14 receives a flow of gas from a gas source, such as the ambient atmosphere, as indicated by arrow A in FIG. 1 and elevates the pressure of that gas for delivery to the airway of subject 12. Pressure generator 14 is any device, such as, for example, a pump, blower, piston, or bellows, that is capable of elevating the pressure of the received gas for delivery to subject 12. The present disclosure also contemplates that gas other than ambient atmospheric air may be introduced into system 10 for delivery to subject 12. In such embodiments, a pressurized canister or tank of gas containing air, oxygen, and/or another gas may supply the intake of pressure generator 14. In some embodiments, pressure generator 14 need not be provided, but instead the gas may be pressurized by the pressure of the canister and/or tank of pressurized gas itself.

In some embodiments, pressure generator 14 is a blower that is driven at a substantially constant speed during the course of the pressure support treatment to provide the pressurized flow of breathable gas with a substantially constant elevated pressure and/or flow rate. Pressure generator 14 may comprise a valve for controlling the pressure/flow of gas. The present disclosure also contemplates controlling the operating speed of the blower, either alone or in combination with such a valve, to control the pressure/flow of gas provided to subject 24.

The pressurized flow of breathable gas is delivered to the airway of subject 12 from pressure generator 14 and/or nebulizer 16 via subject interface 24. Subject interface 24 is configured to communicate the pressurized flow of breathable gas generated by pressure generator 14 and/or humidified by nebulizer 16 to the airway of subject 12. As such, subject interface 24 comprises one or more conduits 28, an interface appliance 30, and/or other components. Conduits 28 are configured to convey the pressurized flow of gas to interface appliance 30. Interface appliance 30 is configured to deliver the flow of gas to the airway of subject 12. In some embodiments, interface appliance 30 is non-invasive. As such, interface appliance 30 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 30. Some examples of non-invasive interface appliance 30 may comprise, for example, a tracheal cannula, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to subject 12 using any interface appliance.

Although subject interface 24 is illustrated in FIG. 1 as a single-limbed circuit for the delivery of the flow of gas to the airway of subject 12, this is not intended to be limiting. The scope of this disclosure comprises double-limbed circuits having a first limb configured to provide the flow of gas to the airway of subject 12, and a second limb configured to selectively exhaust gas from subject interface 24 (e.g., to exhaust exhaled gases).

Sensor 18 is configured to generate output signals conveying information related to one or more parameters of the pressurized flow of breathable gas. Information related to one or more parameters of the pressurized flow of breathable gas may include information related to a flow rate, a volume, a pressure, humidity, temperature, acceleration, velocity, and/or other gas parameters; breathing parameters related to the respiration of subject 12 such as a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters; parameters related to the operation of pressure generator 14, nebulizer 16, and/or other components of system 10; parameters related to the ambient environment, and/or other information. Sensor 18 may comprise one or more sensors that measure such parameters directly (e.g., through communication with the pressurized flow of breathable gas in conduit 28). Sensor 18 may comprise one or more sensors that generate output signals related to the pressurized flow of breathable gas indirectly. For example, sensor 18 may comprise one or more sensors configured to generate an output based on an operating parameter of pressure generator 14, nebulizer 16 (e.g., a current drawn, voltage, and/or other operation/operating parameters), and/or other sensors.

Sensor 18 may include pressure sensors, flow rate sensors, volume sensors, humidity sensors, liquid level sensors, usage time sensors, temperature sensors, external sensors 19, and/or other sensors. External sensors 19 may include, for example, altitude sensors, home heating/cooling mode/settings sensors (e.g., configured to generate output signals conveying information related to home HVAC mode, settings, mode cycle, etc.), room ambient conditions sensors, home exterior ambient conditions sensors, and/or other sensors. Sensors 18 and/or 19 may include a plurality of individual sensors located at various locations throughout system 10, in the immediate sleeping area, in the home and/or positioned to generate information about conditions exterior to the home (e.g., environmental conditions measured by the system and/or retrieved from some other system or database).

FIG. 1 illustrates four different locations for individual sensors 18 and one location of external sensors 19. This is not intended to be limiting. System 10 may include any number of sensors 18 and/or 19 located anywhere within system 10 and/or in proximity to system 10 provided system 10 functions as described herein. For example, sensor 18 may include one or more of pressure, flow rate, humidity, temperature, and/or other sensors in communication with the pressurized flow of breathable gas in conduit 28. Sensor 18 may be and/or include a transducer configured to detect acoustic waves transmitted through subject interface 24. These acoustic waves may convey information related to respiratory effort of subject 12, and/or the noise generated by subject 12 during respiration (e.g., during snoring). Sensor 18 may be and/or include liquid level sensors configured to generate one or more output signals conveying information related to a current liquid level 23 in nebulizer 16.

In this example, sensor 18 may be and/or include one or more of a float switch, a pressure sensor, an ultrasonic sensor, a heat capacity based sensor, and/or other liquid level sensors. Sensor 18 may be and/or include usage time sensors configured to generate one or more output signals conveying information related to one or more usage time parameters. The one or more usage time parameters may comprise parameters related to the total time subject 12 spends connected to system 10 during a usage session, and/or the time subject 12 is asleep while connected to system 10 during a usage session. Sensor 18 may include one or more subject interface temperature sensors configured to generate one or more output signals conveying information related to the temperature of one or more components of subject interface 24. Sensor 18 may include one or more environmental sensors configured to generate output signals related to conditions (e.g., temperature, humidity) of the ambient environment around system 10. At the top of liquid level 23 there is a mesh 52 through which droplets 54 pass.

User interface 20 is configured to receive entry and/or selection of feedback information from subject 12 and/or other users indicating an initial comfort level with the pressurized flow of breathable gas. After an automatic adjustment to the pressurized flow of breathable gas (described below), user interface 20 is configured to receive entry and/or selection of additional feedback information from subject 12 indicating an adjusted comfort level. User interface 20 is configured to provide an interface between system 10 and subject 12 and/or other users (e.g., a doctor, care-giver, etc.) through which subject 12 may provide information to and receive information from system 10. This enables data, cues, results, and/or instructions and any other communicable items, collectively referred to as "information," to be communicated between subject 12 and one or more of pressure generator 14, electronic storage 50, processor 22, and/or other components of system 10. Examples of interface devices suitable for inclusion in user interface 20 comprise a keypad, buttons, switches, a keyboard, knobs, levers, a display screen, a touch screen, speakers, a microphone, an indicator light, an audible alarm, a printer, a tactile feedback device, and/or other interface devices.

It is to be understood that other communication techniques, either hard-wired or wireless, are also contemplated by the present disclosure as user interface 20. For example, the present disclosure contemplates that user interface 20 may be integrated with a removable storage interface provided by electronic storage 50. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 20 comprise, but are not limited to, an RS-232 port, RF link, an IR link, modem (telephone, cable or other). In short, any technique for communicating information with system 10 is contemplated by the present disclosure as user interface 20.

In some embodiments, user interface 20 comprises a plurality of separate interfaces. In some embodiments, user interface 20 comprises at least one interface that is provided integrally with pressure generator 14. In some embodiments, user interface 20 includes one or more of a user interface that is integral with pressure generator 14 and/or a graphical user interface presented to subject 12 via a client computing device (not shown in FIG. 1). For example, user interface 20 may be and/or include a graphical user interface that is presented to subject 12 on a smartphone and/or other computing device associated with subject 12. This may allow subject 12 to provide feedback to system 10, receive feedback from system 10, and/or receive a prompt to make a manual adjustment (for example) during therapy and/or at other times while subject 12 is not in immediate proximity to pressure generator 14 and/or nebulizer 16, for example.

Processor 22 is configured to provide information processing capabilities in system 10. As such, processor 22 may comprise one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some embodiments, processor 22 may comprise a plurality of processing units. These processing units may be physically located within the same device (e.g., pressure generator 14, nebulizer 16, a client computing device), or processor 22 may As shown in FIG. 1, processor 22 is configured to execute one or more computer program components. The one or more computer program components may include one or more of a flow delivery component 40, a nebulizer component 42, a heater component 44, and/or other components. Processor 22 may be configured to execute components 40, 42, and/or 44 by software; hardware; firmware; some combination of software, hardware, and/or firmware; and/or other mechanisms for configuring processing capabilities on processor 22.

It should be appreciated that although components 40, 42, and 44 are illustrated in FIG. 1 as being co-located within a single processing unit, in embodiments in which processor 22 includes multiple processing units, one or more of components 40, 42, and/or 44 may be located remotely from the other components. The description of the functionality provided by the different components 40, 42, and/or 44 described below is for illustrative purposes, and is not intended to be limiting, as any of components 40, 42, and/or 44 may provide more or less functionality than is described. For example, one or more of components 40, 42, and/or 44 may be eliminated, and some or all of its functionality may be provided by other components 40, 42 and/or 44. As another example, processor 22 may be configured to execute one or more additional components that may perform some or all of the functionality attributed below to one of components 40, 42, and/or 44.

In some embodiments, flow delivery component 40 is configured to cause pressure generator 14 to deliver a flow of breathable gas to the subject. Nebulizer component 42 is configured to cause nebulizer 16 to provide moisture to the breathable gas. Heater component 44 is configured to cause heater 38 to heat a volume of the breathable gas before moisture and/or droplets are supplied to the breathable gas. Advantageously, supplying warm air with a temperature above body core temperature results in less heat and water vapor loss from the subject's upper trachea with respect to prior systems. As mentioned herein, a comparatively cold and therefore dry air inflow, as seen in prior systems, will induce a marked heat and vapor flow from the skin of the upper trachea of the subject. The skin of the upper trachea will thus be cooled and dried out. This may lead to discomfort and an increased risk of infection and ciliary dysfunctionality. The droplets might not be able to prevent the drying out of the tracheal skin because only a small fraction (e.g. 10-30%) of the droplets will be deposited at the trachea surface. In some embodiments according to the present technology, a reduced diameter of droplets is achieved, which gives the droplets a much higher probability of reaching the airways without hitting the walls of the tracheal cannula bend.

It is not advantageous to heat up the breathable gas after the moisture and/or droplets application because this process would take too long. An advantage in heating up the breathable gas before it reaches nebulizer 16 is that the time needed to evaporate droplets 54 is much shorter and thus the required minimum distance between nebulizer 16 and subject interface 20 is much smaller (a short distance d, e.g., between about 1 cm and 30 cm, although all other appropriate distances are contemplated). That is one of the advantages of this design. The temperature gradient between the heated air and cold droplets 54 is high and therefore droplets 54 evaporate quickly. If you want to heat the mixture of air plus droplets 54, then the temperature gradient between the air surrounding droplets 54 and droplets 54 themselves is much smaller and therefore the evaporation takes longer.

A drawback of prior art "heated humidification" is that the device cannot be placed close to the subject's trachea, because it is heavy and bulky, contains an open water reservoir, etc. Instead a "heated humidifier" is connected to the patient via more than one meter of tubing. Inside this tubing, water condensation will occur, since it is very difficult to hold this long tubing at an elevated temperature. After some time, the tubing will contain appreciable amounts (up to several tens of ccm) of water. There is a risk of aspiration by the subject. In contrast, some embodiments according to the present technology advantageously only heat the room air and add water droplets close to the subject's trachea, so that the long tubing to the subject remains dry.

In some embodiments, choosing a fixed, reasonable distance between the nebulizer and a subject and controlling operation/operating parameters (e.g., temperature, flow velocity, droplet size, heating power, etc.) is accomplished in a way that an equilibrium between air and droplets 54 is established within this distance. "Equilibrium" as used herein mean that no water is further evaporated (or condensed) from the droplets. A fast heating device (low-mass wire on high temperature) is implemented so that the heating power could be adjusted proportionally to the air flow velocity of the breathing pattern during inspiration.

In some embodiments, the tracheal cannula (conduit 28) has a bend, as mentioned herein. The tracheal cannula is communicatively coupled with pressure generator 14 (e.g., a ventilator). The tracheal cannula has an inner lumen diameter and the bend of the tracheal cannula has a curvature radius. The tracheal cannula is configured to supply the breathable gas to the airway of subject 12. The inner lumen diameter and the curvature radius facilitate the delivery of droplets to the trachea of subject 12 such that the breathable gas received by subject 12 exhibits a target temperature and humidity level. In some embodiments, the target temperature of about room temperature and a relative humidity are maintained at an interface (such as interface appliance 30) to the subject, the relative humidity being about 100%.

In some embodiments, the inner lumen diameter falls within a range of about 4 mm to about 11 mm. These are merely exemplary ranges, and all other suitable ranges are contemplated. In some embodiments, the curvature radius falls within a range of about 17 mm to about 25 mm. These are merely exemplary ranges, and all other suitable ranges are contemplated. In some embodiments, the moisture may be in the form of a mist of water droplets. The temperature of the breathable gas at the subject interface ranges from about room temperature to a maximum permitted temperature of 42° C. in some embodiments. Regarding humidity levels, the total water content (water vapor and water droplets) of the gas entering the subject interface should fall within the range of about 20 mg/L to about 44 mg/L, in some embodiments. In some embodiments, the mist may also be from a saline solution.

In some embodiments, mesh 52 is a vibrating mesh nebulizer. Vibrating mesh nebulizers are known in the art. One exemplary vibrating mesh nebulizer that may be used in some embodiments of the present technology is manufactured by Aerogen, Inc. An example of a patent application related to a vibrating mesh nebulizer that is assigned to Aerogen, Inc. is US2007/0209659, which is incorporated herein by reference. Mesh 52 is located in nebulizer 16 to generate a mist of water droplets 54 of a defined diameter in the range of about 2 μm to about 8 μm. A fast temperature sensor is located at an entrance of the tracheal cannula to facilitate controlling operating conditions including temperature, humidity, and other conditions mentioned in this disclosure. Fast temperature sensors are known in the art and exhibit fast response/reaction times to changes in temperature. The fast temperature sensor is configured to trigger a switch-off of heater 38 when a threshold temperature is reached at the entrance of the tracheal cannula indicating that nebulizer 16 is failing to produce droplets. The threshold temperature would be set within the range of about 40° C. to about 42° C. (current standards are limiting the temperature of an air stream to human airways to be less or equal 42° C.).

Processor 22 is configured to determine one or more parameters related to the pressurized flow of breathable gas. Processor 22 is configured to determine the one or more parameters based on the output signals from sensor 18 and/or other information. The one or more parameters related to the pressurized flow of breathable gas may comprise, for example, one or more of a flow rate, a volume, a pressure, humidity of the gas, temperature of the gas, acceleration, velocity, ambient temperature, a relative ambient humidity, leak, the humidification method, humidification method set points (e.g., a target humidity level, heater plate temperature, etc.), a subject interface (e.g., conduit) temperature, water usage (e.g., per hour and/or per session), altitude, home heating/cooling mode/settings, and/or other parameters. In some embodiments, processor 22 is configured to obtain operational status indicators generated by pressure generator 14 and/or nebulizer 16, for example, that indicate an operational status of the individual component. The operational status indicators may indicate, for example, whether individual devices within a given component are operating as expected. For example, heater 38 of nebulizer 16 provides heat when required. The information determined by processor 22 may be used to control system 10 according to a predetermined therapy regime, adjust the therapy provided to subject 12, determine whether to prompt subject 12 and/or other users to manually adjust one or more components of processor 22, and/or for other uses.

Processor 22 is configured to control pressure generator 14, nebulizer 16, and/or other components to deliver the pressurized flow of breathable gas to subject 12. Processor 22 is configured to control pressure generator 14, nebulizer 16, subject interface 24, and/or other components according to a predetermined therapy regime. Processor 22 is configured to control pressure generator 14, nebulizer 16, subject interface 24, and/or other components based on the output signals from sensor 18, information determined by parameter component 40, and/or other information. By way of a non-limiting example, processor 22 may control pressure generator 14 such that the pressure support provided to subject 12 via the flow of gas comprises non-invasive or invasive ventilation, positive airway pressure support, continuous positive airway pressure support, bi-level support, BiPAP®, and/or other types of pressure support therapy.

In some embodiments, processor 22 is configured such that the predetermined therapy regime is based on typical ambient weather conditions during a given season of the year, previous feedback information from subject 12 received during the given season, information from a thermostat controlling the temperature of the environment where pressure support therapy occurs, and/or other information. Processor 22 may be configured to wirelessly (and/or via wires) communicate with external resources via a network (e.g., the Internet) to obtain such information. For example, processor 22 may determine the season of the year based on information retrieved from an external server that stores information related to the ambient weather. Processor 22 may obtain previous feedback information from subject 12 that is stored in electronic storage 50, for example, and/or in other locations. The information may be stored in electronic storage 50 with identifiers that convey when the information (e.g., the date) was received and/or stored, for example. Processor 22 may retrieve information from the thermostat controlling the temperature of the environment via a local area network and/or other networks, for example.

Processor 22 is configured to receive feedback information entered and/or selected through user interface 20. Processor 22 is configured to receive entry and/or selection of feedback information from subject 12 indicating an initial comfort level with the pressurized flow of breathable gas. After an automatic adjustment to the pressurized flow of breathable gas (described herein), processor 22 is configured to receive entry and/or selection of additional feedback information from subject 12 indicating an adjusted comfort level. In some embodiments, processor 22 is configured to control user interface 20 to present one or more views of a graphical user interface to subject 12 that facilitate entry and/or selection of the feedback information. In some embodiments, the feedback information includes information related to an inhaled air temperature, an inhaled air moisture, whether or not subject 12 has experienced tube rainout, whether or not subject 12 has experienced mask rainout, and/or other information.

In some embodiments, processor 22 may be configured such that the one or more views of the graphical user interface presented to subject 12 via user interface 20 facilitate rating at least some portions of the feedback information according to a predetermined ratings scale. For example, processor 22 may facilitate rating the inhaled air temperature (e.g., 0 being too cold, 10 being too hot), rating the inhaled air moisture (e.g., 0 is too dry, 10 is too wet), and/or rating other factors.

Processor 22 is configured to make an automatic adjustment to the pressurized flow of breathable gas to enhance the comfort level of subject 12. The automatic adjustment may be made based on the received feedback, the output signals from sensor 18, the information determined by various components, and/or other information. The automatic adjustment may include adjustment of pressure generator 14, nebulizer 16, subject interface 24, and/or other components of system 10.

In some embodiments, as described above, user interface 20 and/or processor 22 is configured to receive additional feedback information entered and/or selected through user interface 20 subsequent to an automatic adjustment. In some embodiments, additional automatic adjustments are made to the pressurized flow of breathable gas to enhance the comfort level of subject 12. The additional automatic adjustment may be made based on the additional feedback information, the output signals from sensor 18, the information determined by processor 22, and/or other information.

The additional automatic adjustment may include adjustment of pressure generator 14, nebulizer 16, subject interface 24, and/or other components of system 10. In some embodiments, processor 22 is configured such that the adjustment, feedback, adjustment process is repeated (e.g., iterated) one or more times. Processor 22 may be configured to repeat the adjustment and feedback cycle when the feedback information indicates that the comfort level of subject 12 is improving, for example. In some embodiments, processor 22 is configured to cease automatic adjustments responsive to the feedback information indicating that subject 12 is comfortable, the feedback information indicating that the comfort level of subject 12 is not improving (e.g., the temperature of the inhaled air is still too cold for subject 12, rainout still occurs even after all of the automatic adjustments, etc.), and/or for other reasons.

Processor 22 is configured to determine whether to prompt subject 12 and/or other users to make a manual adjustment to system 10 and/or external factors associated with system 10. Processor 22 may be configured to control user interface 20 to prompt subject 12 and/or other users.

The manual adjustment may include, for example, manual adjustments to one or more components of system 10, manual adjustments to the ambient environment, manually adjusting the therapy location, and/or other manual adjustments. A manual adjustment may include an adjustment to pressure generator 14, nebulizer 16, subject interface 24, and/or other components of system 10.

In some embodiments, the prompted manual adjustment includes changing the temperature of the ambient environment, changing a type of therapy of the predetermined therapy regime, changing physical components of the pressure support system (e.g., adding and/or removing a heater for conduit 28), changing the tank capacity of nebulizer 16, changing a mask (e.g., interface appliance 30) that has excessive leak), and/or other manual adjustments. In some embodiments, the manual adjustments include manually changing therapy set points (e.g., target humidity level, target temperature, etc.) via user interface 20, for example.

Processor 22 is configured to determine whether to prompt subject 12 and/or other users based on the additional feedback information subsequent to the automatic adjustment, the output signals from sensor 18, the information determined by various components, the automatic adjustments to the pressurized flow of breathable gas, and/or other information.

In some embodiments, processor 22 is configured such that subject 12 and/or other users are prompted to make a manual adjustment only if necessary. Subject 12 and/or other users may be prompted to make a manual adjustment if the automatic adjustment to the pressurized flow of breathable, for example, gas does not enhance the comfort level of subject 12, does not enhance the comfort level by a predetermined amount, and/or for other reasons. For example, processor 22 may be configured to prompt subject 12 to try a different pressure generator, nebulizer, and/or subject interface (e.g., prompt a switch from a subject interface that does not include a heater to one that does include a heater), and/or run a system diagnostic if the present components of system 10 are unable to be adjusted enough to satisfy the needs of subject 12.

The description of an automatic adjustment by processor 22 and then, if necessary, a prompted manual adjustment is not intended to be limiting. In some embodiments, processor 22 is configured to prompt subject 12 and/or other users to make a manual adjustment before any automatic adjustment by processor 22. In these embodiments, processor 22 may not make an automatic adjustment at all and/or make an automatic adjustment only after processor 22 prompts manual adjustment.

In some embodiments, processor 22 is configured to provide feedback to subject 12 via user interface 20 and/or other components of system 10. For example, processor 22 may be configured to notify subject 12 if a component(s) obtains operational status indicators that indicate, for example, that individual devices within a given component are not operating as expected (e.g., heater 38 of nebulizer 16 does not provide heat when required, sensor 18 is out of range, expected leak is out of range, environmental conditions exceed system capabilities, pressure generator 14 malfunctions, and/or feedback components are unavailable.)

Figure 2:
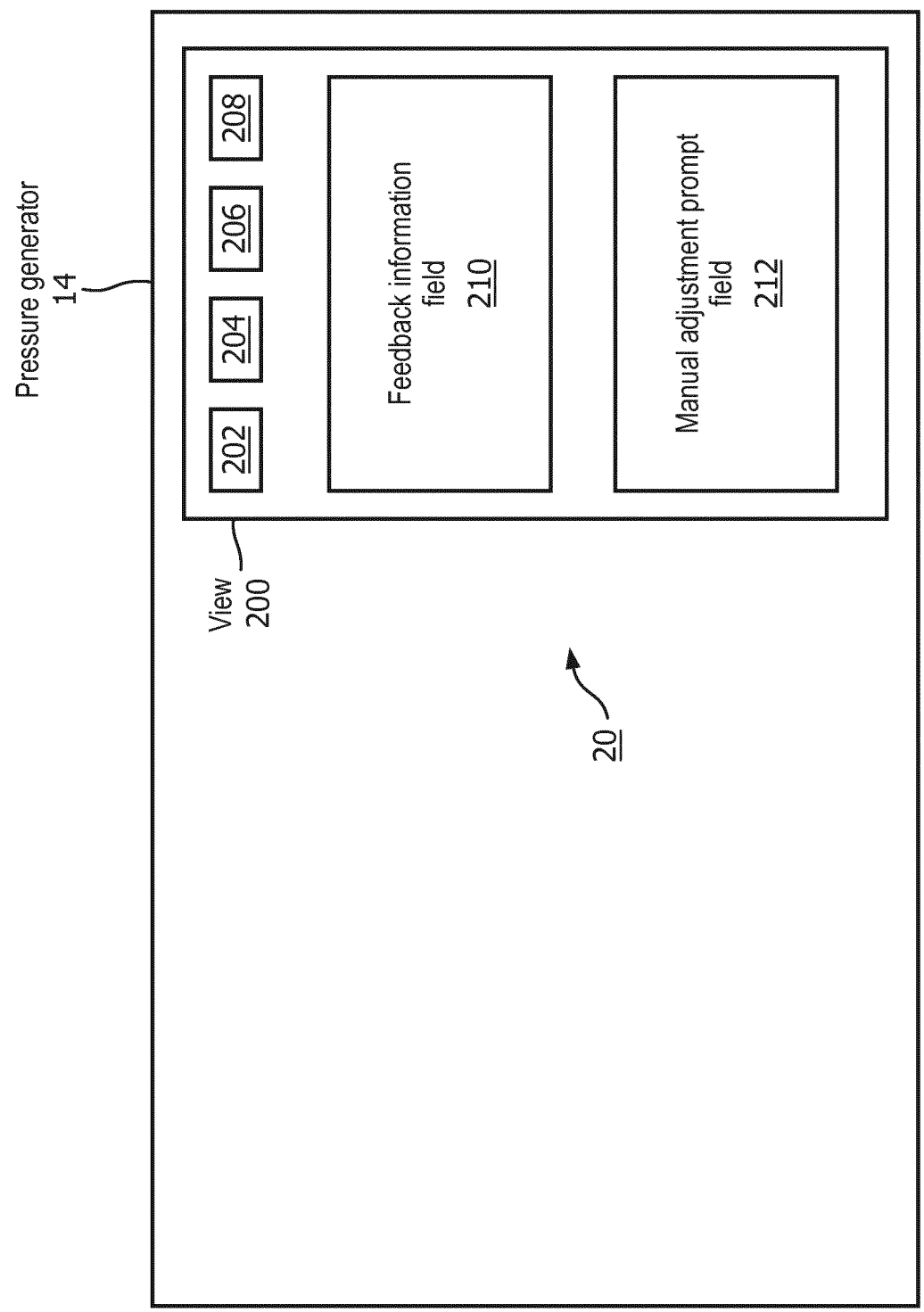

By way of a non-liming example, FIG. 2 illustrates of a view 200 of user interface 20 presented to subject 12 (FIG. 1) and/or other users. In FIG. 2, user interface 20 is integral with pressure generator 14. View 200 includes parameter fields 202, 204, 206, and 208, a feedback information field 210, and a manual adjustment prompt field 212. One or more components of processor 22 may control user interface 20

(as described above) to provide information to and/or receive information from subject 12 and/or other users. For example, one or more parameters determined by parameter component 40 may be displayed to subject 12 via parameter fields 202-208. Parameters such as ambient temperature, ambient relative humidity, the type of pressure support therapy and/or humidification, pressure support therapy and/or humidification set points, leak, an operational status indicator (e.g., indicating whether components of system 10 are operating normally), and/or other parameters.

Feedback information field 210 is configured to receive entry and/or selection of feedback information from subject 12 and/or other users. Field 210 may be touch sensitive (e.g., a touchscreen) so that subject 12 and/or the other users may enter information by touching field 210. Field 210 may display information entered via a keyboard, keypad, and/or other entry device.

Manual adjustment prompt field 212 may be configured to display prompts to the user to facilitate adjustment of system 10, make recommendations to subject 12, and/or provide other information. For example, field 212 may display messages such as, "Increase the room temperature," and/or, "Change to a subject interface that includes a heated tube," and/or other informational messages. Recommendations may be related to, for example, the pressure support therapy and/or humidification method, pressure support therapy and/or humidification method set points, and/or other information.

Figure 3:
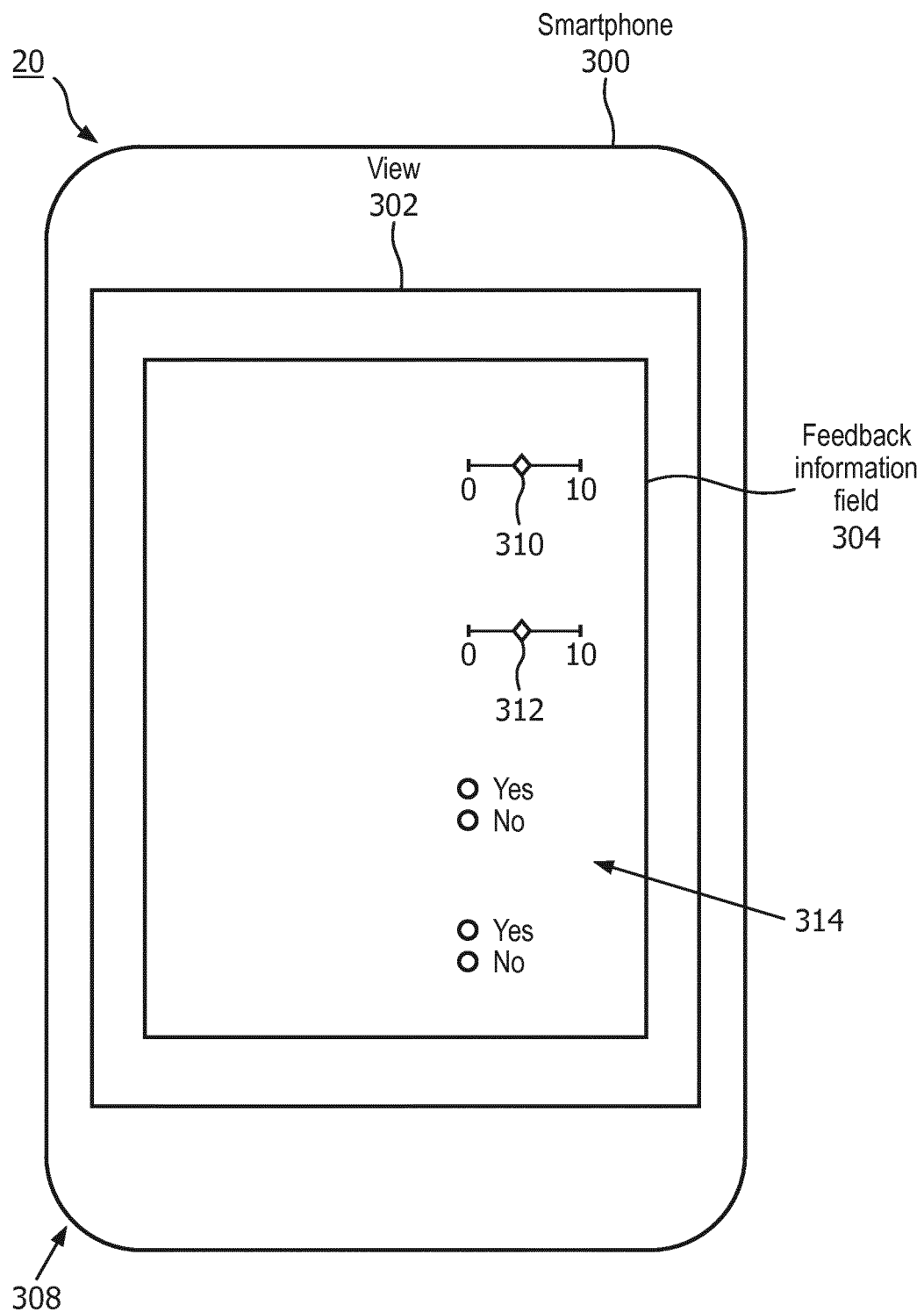

By way of a second non-limiting example, FIG. 3 illustrates a view 302 of user interface 20 presented to subject 12 (FIG. 1) and/or other users via a display of a smartphone 300 and/or other mobile computing device associated with subject 12. View 302 includes feedback information field 304. In the example shown in FIG. 3, processor 22 (FIG. 1) has controlled field 304 to display survey questions 308. The survey questions are configured to facilitate entry and/or selection of information related to the comfort level of subject 12 during therapy. In the example shown in FIG. 3, subject 12 may provide information by dragging and dropping an indicator 310, 312 on a scale of 1 to 10, and/or activating YES/NO indicators 314. These options are not intended to be limiting. Processor 22 may control field 304 to facilitate entry and/or selection of comfort level information in any way that allows system 10 to operate as described herein.

Figure 4:
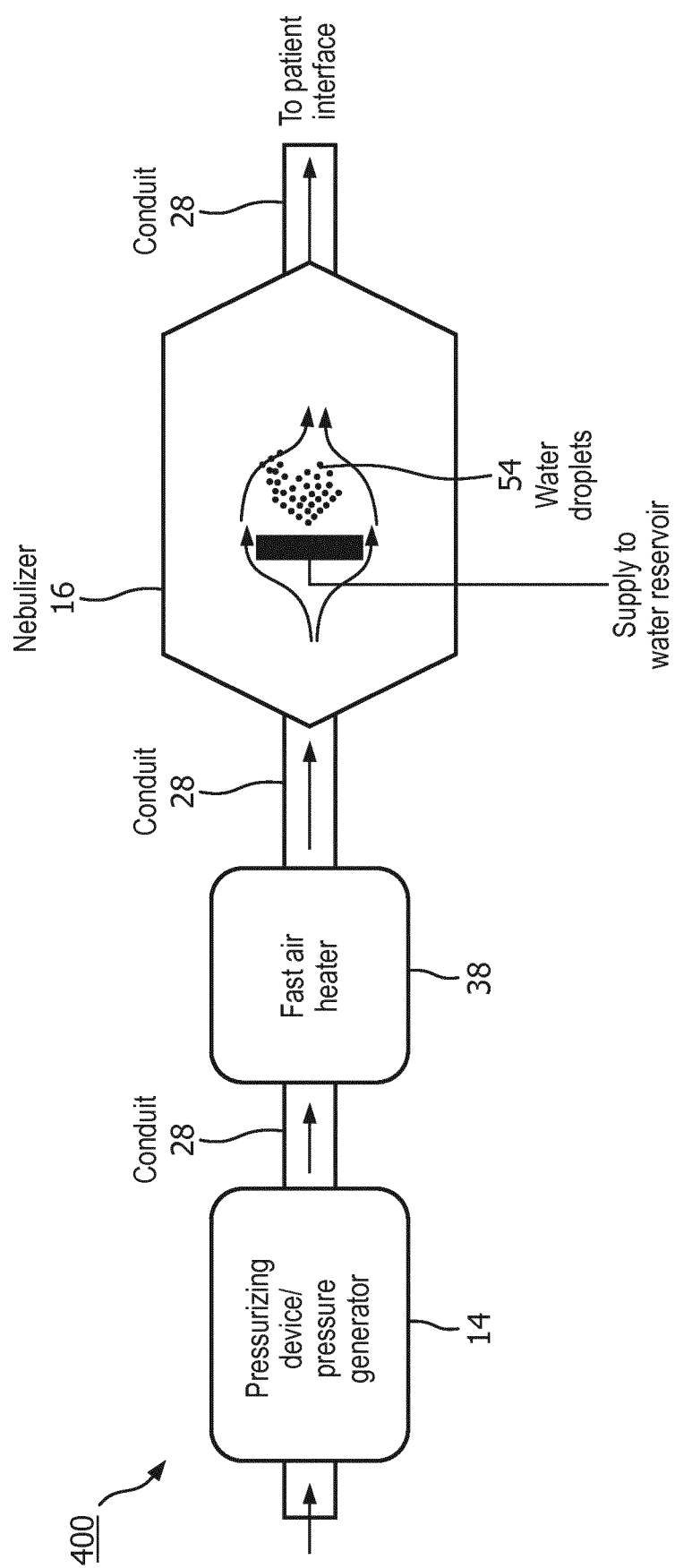

FIG. 4 illustrates a system 400 configured to facilitate humidification of a pressurized flow of breathable gas delivered to a subject. System 400 is similar to system 10 of FIG. 1. Pressure generator (pressurizing device) 14 is communicatively coupled with (fast air) heater 38. In some embodiments, as illustrated, conduit 28 passes through heater 38. Nebulizer 16 includes vibrating mesh nebulizer 52 that is communicatively coupled with a supply to a water reservoir. Water droplets 54 are emitted from vibrating mesh nebulizer 52.

Figure 5:
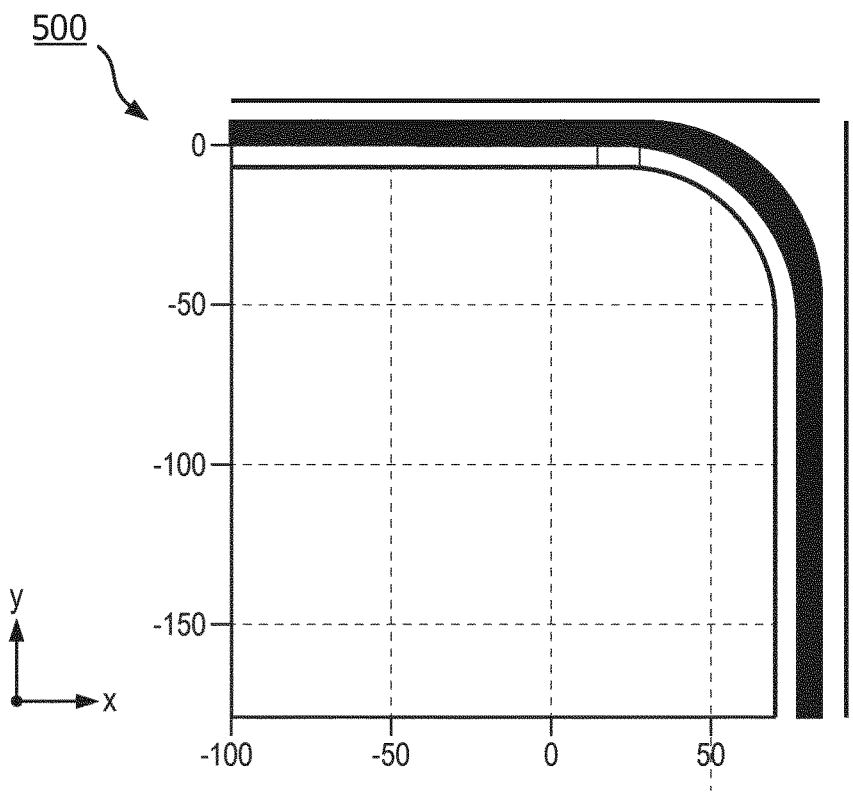
Figure 6:
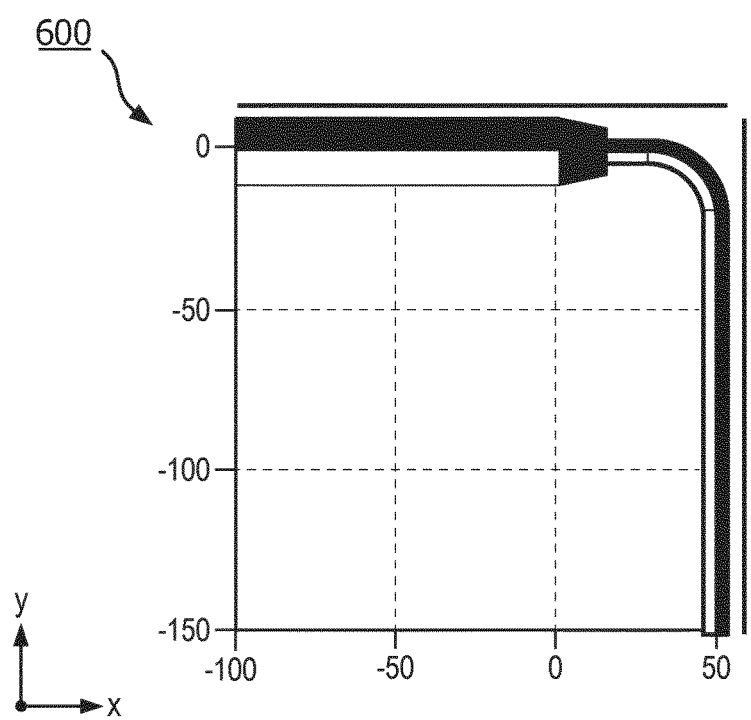

FIG. 5 illustrates a simulation model of a personal nebulizer 500 of system 10. In some embodiments, personal nebulizer 500 may include one or more of the tracheal cannula, conduit 28, subject interface 24, interface appliance 30, and/or other elements. The vertical portion of the tube represents a trachea. The numbers shown indicate millimeters. The model is isothermal at 20° C.; the reference pressure is 1 atm. The inner tube diameter is 16 mm; the curvature radius of the bend is 50 mm. Air is entering from the left at a peak flow rate of 70 L/min. The vertical tube represents the trachea. The overpressure at its lower end (the outlet) is set to zero. As a first study a stationary laminar flow solution is calculated. The entrance overpressure is 0.09 mbar (9 Pa); the average flow velocity at the outlet/inlet is 5.90 m/s. The Reynolds number for this peak flow is 6100; therefore the assumption of laminar flow is not justified, since purely laminar flow can be generally assumed (in the case of tubes) for Reynolds numbers <2300 and turbulent flow has to be assumed for Rey >4000. Nevertheless laminar flow calculations were performed for simplicity reasons. The pressure moving from the left end to the lower end ranged from about 0.76 mbar to about 0.00 mbar.

As a second study a simulation was performed that is referred to as "Particle Tracing for Fluid Flow." 100 uncharged spherical particles (water droplets) were released at the air inlet at t=0 with a homogeneous distribution over the inlet surface. Their initial velocity was the flow velocity; their density was 1 kg/L, and their diameter was 5 μm. These droplets are then followed in time under influence of a Stokes drag force. If a droplet would hit a wall, it would stick to the wall with 100% probability. Droplets reaching the outlet were recorded there with their velocity. In the simulation, 21 droplets hit a wall and 79 droplets have reached the outlet. The simulated transmission probability was thus 79%.

FIG. 6 illustrates a simulation model of a personal nebulizer 600 of system 10. In some embodiments, personal nebulizer 600 may include one or more of the tracheal cannula, conduit 28, subject interface 24, interface appliance 30, and/or other elements. The numbers shown indicate millimeters. The simulation is related to the geometry of the 22 mm inner diameter supply tube, a conical connector piece (15 mm long, final diameter 16 mm) and a "Tracheoflex S" trach with an 8 mm inner diameter. The trach length dimensions are: intratracheal tubular part A=32.5 mm, extratracheal tubular part B=12.7 mm, bent length C=31.4 mm, trach angle q=90° (for geometrical simplicity; true angle is 95°). After 0.5 s, 12 droplets have hit a wall, 1 droplet is still in the tube volume, and 8 droplets are lost. Air is entering from the left at a peak flow rate of 70 L/min. The vertical tube represents the trachea. The overpressure at the lower end (the outlet) is set to zero. As a first study a stationary laminar flow solution was calculated. The entrance overpressure was 8.39 mbar; the average flow velocity at the inlet was 3.10 m/s, the average flow velocity at the outlet was 24.3 m/s. The peak flow Reynolds number is 12200. Therefore the assumption of laminar flow is not justified anymore. Nevertheless (for simplicity reasons) a laminar flow calculation was performed. The pressure moving from the left end to the lower end ranged from about 8.2 mbar to about 0.03 mbar. The air velocity moving from the left end to the lower end ranged from less than 5 m/s to over 30 m/s.

In a second study a simulation referred to as "Particle Tracing for Fluid Flow" was performed. 100 uncharged spherical particles water droplets) were released at the air inlet at t=0 with a homogeneous distribution over the inlet surface. Their initial velocity is the flow velocity, their density was 1 kg/L, and their diameter was 5 μm. These droplets were then followed in time under influence of a Stokes drag force. If a droplet will hit a wall, it would stick to the wall with 100% probability. Droplets reaching the outlet were recorded there, with their velocity. After 0.2 s, 98 droplets hit a wall, whereas only 2 droplets reached the outlet. The simulated transmission probability was thus 2%.

System 10 can be simulated using a droplet model based on Newtonian inertia and a Stokes drag force. Other mechanisms such as droplet growth by water vapor condensation or droplet coagulation apparently do not play a role. This seems reasonable, because these are comparatively "slow"

processes, whereas the time scale for the observed disappearance of 5 µm droplets is in the order of 1 ms (0.01 m/(10 m/s)) (i.e. quite "short"). After 0.5 s, 6 droplets have hit the conical connector wall, 26 droplets have hit the "step" between the connector and trach, 62 droplets have hit the "trach" walls, 1 droplet is still in the volume of the supply tube, and 3 droplets are "lost."

The Stokes drag force for spherical particles in low Reynolds number flows is $$F_s = 6\pi \cdot \mu \cdot \frac{d_p}{2} \cdot (v_F - v_p)$$

where µ=air dynamic viscosity (1.86E-5s*Pa at 25° C.), $d_p$=particle diameter (5 µm), $v_F$=fluid velocity vector [m/s], $v_p$=particle velocity vector [m/s]. In Comsol this is written as $$F_s = \frac{m_p}{\tau_p} \cdot (v_F - v_p)$$

with the "particle velocity response time"

$$\tau_p = \frac{\rho_p \cdot d_p^2}{18\mu} = 0.075 \text{ ms } (\rho_p = \text{particle density}(1 \text{ kg/L})).$$

For a maximum gas/particle velocity of 30 m/s this is corresponding to a distance travelled of 2.2 mm. It will take a certain multiple (≈3) of "response times" (or, respectively, a distance travelled $\Delta x_{equal}$≈7 mm) before gas and particle velocities are really "identical".

Thus, a first consequence of this "short" particle velocity response time is that the droplets will be accelerated to the suddenly increased gas velocity at the trach entrance (where the velocity vectors of gas and particle are parallel) within few tenths of a millisecond, i.e. within less than a cm distance travelled.

What is happening in the bend of the trach should be considered. It can be noticed that the distance $\Delta x_{equal}$≈7 mm is already 34% of the curvature radius of the bend (20mm). Therefore, one may expect that a large fraction of the droplets will have problems to traverse the bend without hitting the right wall.

Looking at the distribution of gas velocity vectors in the trach, the gas flow is "squeezed" towards the right wall when traversing the bend. This means that the gas velocity vectors will remain nearly parallel to the horizontal axis for a long time (i.e. until x≈35 mm) before developing a component in the -y direction. This is especially true for particles above the center line y=0 (the middle of the left opening). For those particles the -y component of the Stokes drag force is too small to "bend" their particle velocity vector before the particle hits the tube wall.

This is confirmed if one looks at the traces of the 2 particles that are eventually transmitted. It is easily seen that these particles are the ones entering the trach with the lowest possible y-coordinate so that they will experience a considerable Stokes drag force component in -y direction during a long distance so that they are just able to avoid a collision with the "right" wall.

For a geometry referred to as "Uniform tube radius & large curvature radius of bend", the situation is much more favorable for the droplets. The maximum gas/particle velocity is now ≈7 m/s, which implies that the "particle velocity response time"

$$\tau_p = \frac{\rho_p \cdot d_p^2}{18\mu} = 0.075 \text{ ms}$$

is now corresponding to a distance travelled of 0.52 mm.

As stated above it will take a certain multiple (≈3) of "response times" (or, respectively, a distance travelled $\Delta x_{equal}$≈1.6 mm) before gas and particle velocities are really "identical." This distance travelled is only 3% of the curvature radius of the bend (50 mm); therefore the majority of the droplets will now be able to bend down before hitting the right wall.

For a "trach"-like geometry with "suddenly decreasing tube radius & small curvature radius of bend," a large fraction of droplets (~98%) will hit the tube wall at the trach entrance and at the trach bend.

The physical mechanism needed to explain the droplet trajectories is just Newtonian inertia and a Stokes drag force. "Slower" mechanisms like droplet growth by water vapor condensation or droplet coagulation do not play a role.

The fraction of droplets hitting the bend of the trach is a monotonously increasing function of the ratio of $\Delta x_{equal}$ (the distance travelled before gas and particle velocities are equal) to the bend curvature radius. For $\Delta x_{equal}$ one may use the estimate $\Delta x_{equal}$≈3*$v_{max}$*$\tau_p$ where $v_{max}$=maximum gas velocity and $$\tau_p = \frac{\rho_p \cdot d_p^2}{18\mu}.$$

The preceding considerations can be cast into a practical guideline to avoid that a large fraction of droplets is hitting the wall: Define an "impaction criterion" (IC) which should be less than one, if most of the droplets should be transmitted through a certain bend within the tube:

a. $IC = \dfrac{d_p^2 \cdot \phi}{D_t^2 \cdot R_c \cdot 5.E-6 \text{ L/(min·cm)}} < 1,$ where $d_p$=droplet diameter, Φ=air flow, $D_t$=tube diameter, $R_c$=tube bend curvature radius.

In the example of FIG. 5 (as discussed above) we have $d_p$=5 µm, Φ=70 L/min, $D_t$=16 mm, $R_c$=50 mm and thus IC=0.273 which is fulfilling the limiting condition IC<1. This is consistent with our FEM simulation which resulted in 79% transmission probability of those droplets.

Figure 7:
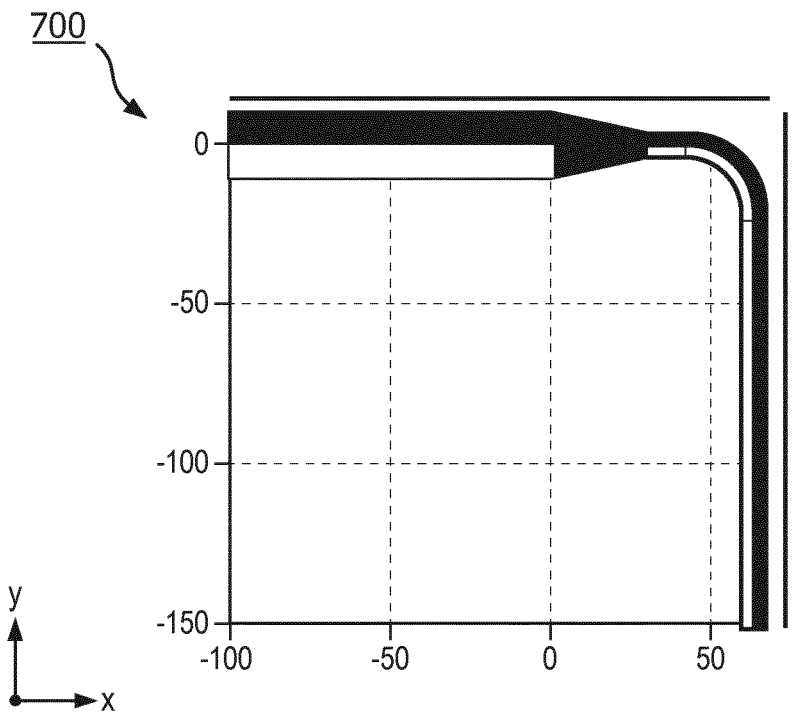
Figure 8:
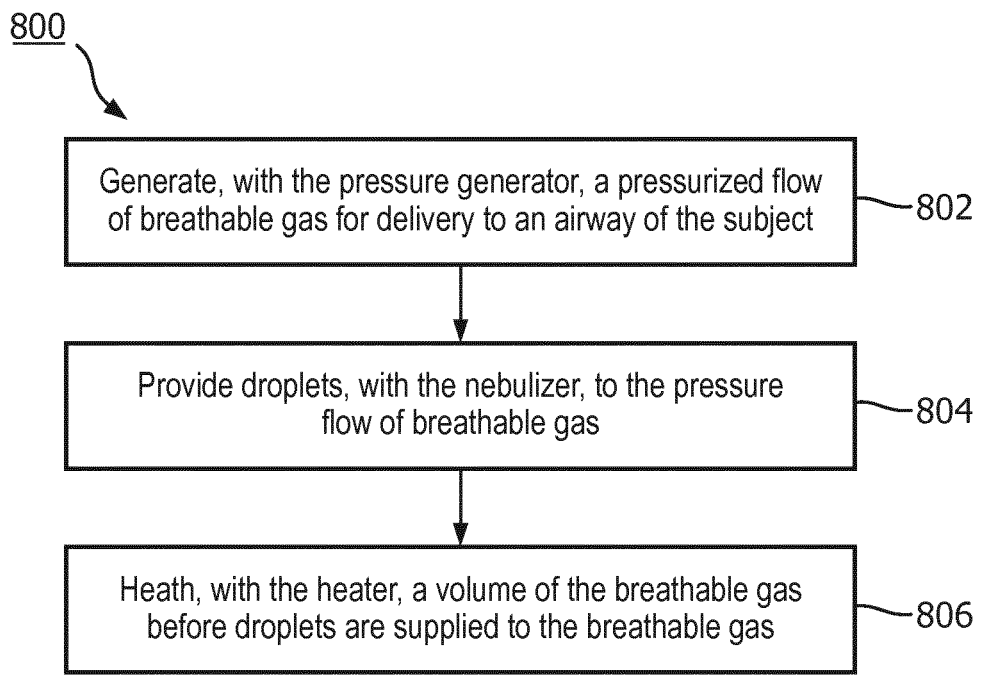

FIG. 7 illustrates a simulation model of a personal nebulizer 700 of system 10. In some embodiments, personal nebulizer 700 may include one or more of the tracheal cannula, conduit 28, subject interface 24, interface appliance 30, and/or other elements. The numbers shown indicate millimeters. This geometry can be referred to as a "smoothly decreasing tube radius and small curvature radius of bend."

The pressure distribution (entrance over-pressure is 7.38 mbar) ranges from about 7.22 mbar at the left entrance to about 0.04 mbar at the bottom outlet. The average flow velocity at the inlet is 3.10 m/s. The average flow velocity at the outlet is 24.3 m/s.

The particle positions after 0.2 s were examined. Out of 100 droplets, 26 droplets reached the outlet. Thus, the transmission probability is 26% (compared to 2% in a prior simulation mentioned herein). The detailed distribution of the other droplets after 0.5 s is that 21 droplets hit the conical connector walls; 43 droplets hit the "trach" walls; 0 droplets are still within the gas volume, and 10 droplets are "lost."

Various simulations have been performed with respect to some embodiments of a personal nebulizer according to the present technology. Some of these simulations related to the evaporation behavior of droplets.

A summary of some simulations that have been performed for system 10 and the operation thereof, including the personal nebulizer of system 10, include:

(1) A simulation was performed using a macroscopic model of water vapor diffusion and heat conduction assuming thermodynamic equilibrium of water vapor and liquid water at the droplet's surface. "Macroscopic" means that no individual droplets have been considered. Instead, the mist of droplets is seen as one homogeneous medium. Water vapor diffusion and heat conduction are strongly coupled by "instantaneous" evaporation/condensation as long as there are droplets. The water droplets just increase the effective "diffusivity of heat" by a certain amount (~12%).

(2) A "particle tracing" FEM model of particle movement in a "dry" air flow of constant temperature. Here the aim was to find the fraction of water droplets hitting the tube wall in a bend. Simple physics (inertia and drag force) were included in the simulation, but a full 3D geometry was simulated. This special model is separated from the others.

(3) An FEM study of temperatures, flow velocities, water vapor in a rotationally symmetric "trachea" (cylinder) with surrounding tissue. A simple geometry was used, but a complete breathing pattern (inhalation and exhalation) was simulated. There were no water droplets added to the gas stream. During inhalation the temperature and humidity of the inhaled air stay almost constant. The (upper) trachea walls deliver only a small fraction of the total amount of heat and water vapor that is transferred to the inhaled and exhaled air volume. The largest part is of these heat and moisture losses is brought up by the lower airways.

Droplets injected into room air are generally not in equilibrium with the gas. Usually there will be water vapor diffusion from the droplets and heat transfer from the surrounding gas, and one will numerically analyze these coupled phenomena in a spherical (1D) Mathcad model describing the transport phenomena in the volume occupied by one droplet. The addressed questions include the following.

It was found that there are actually two time scales: a) rapid evaporation and cooling of a droplet until equilibrium at its surface is established; and b) slower water vapor diffusion from the droplet surface and heat transfer from the gas to the droplet surface.

Regarding final temperature and water vapor concentration, a certain amount of water vapor will evaporate from each droplet. This will lead to a temperature decrease of the droplet (and its surrounding gas), because the water evaporation enthalpy has to be brought up. In the final situation, the water vapor concentration $n_f$ is at equilibrium with the final temperature $T_f$ and the total heat gained by cooling is equal to the total evaporation enthalpy of the evaporated water molecules. This gives a system of two equations with two unknowns ($n_f$ and $T_f$):

$$n_f \cdot k_B \cdot T_f = p_v(T_f) \quad \Delta H(T_a) \cdot \frac{n_f - n_r}{N_A} = (T_r - T_f) \cdot C_{pt}(T_a)$$

Where $p_v(T)$=water vapor pressure [Pa], $\Delta H(T_a)$=water evaporation enthalpy [44.1 kJ/mol] evaluated at an average temperature $T_a$=23° C., $T_r$=supplied air temperature, $n_r$=supplied air water vapor density [1/m$^3$], $C_{pt}(Ta)$=total heat capacity of droplets and air [1311 J/K/m$^3$].

The following is an example: $T_r$=20° C., $n_r$=3.68*10$^{23}$ [1/m$^3$] (=11 mg/L) →$T_f$=15.59° C. and $n_f$=4.47*10$^{23}$ [1/m$^3$] (=13.4 mg/L).

The air temperature will thus decrease by 4.4 K and the water vapor concentration will increase by 21%.

Regarding the volume occupied per droplet, the initial mass of one water droplet is $$m_d = 1\frac{\text{kg}}{\text{L}} \cdot \frac{4}{3}\pi\left(\frac{D_d}{2}\right)^3 = 6.545 \cdot 10^{-8} \text{ mg}.$$

The initial number of water molecules in one droplet is thus $$N_d = \frac{m_d}{18 AMU} = 2.19 \cdot 10^{12}.$$

The initial droplet concentration is $c_i$=33 mg/L. The initial density of water droplets is thus $n_l$=$c_i/m_d$=5.04*10$^8$ droplets/L. The gas volume "occupied" by one droplet is thus $$V_{occ} := \frac{1}{n_1} = 1.983 \times 10^{-9} \text{ L}$$

The number of molecules evaporated from one droplet is thus $$N_{evap} := (n_f - n_r) \cdot V_{occ} = 1.563 \times 10^{11}$$

This is about 7.1% of the initial number of molecules in one droplet $N_d$.

Regarding the time scale of evaporation and condensation, this time scale can be obtained by simple arguments from the kinetic theory of gases:

The collision rate Z [1/s] of water molecules with a certain water droplet is:

$$Z = n \cdot Q \cdot v_{re}$$

where n=density of water molecules [1/m$^3$], Q=collision cross-section=cross-section of water droplet [m$^2$], $v_{rel}$=relative velocity of molecule and droplet=thermal velocity of water molecules [m/s].

At 20° C. room temperature there is a water vapor equilibrium density of $$n_e := \frac{p_v(T_r)}{k_B \cdot T_r} = 5.796 \times 10^{23} \cdot \frac{1}{\text{m}^3}$$

The cross-section of a water droplet with diameter $D_d$=5 μm is $$A_d := \pi \cdot \left(\frac{D_d}{2}\right)^2 = 1.963 \times 10^{-11} \text{m}^2$$

The thermal velocity of the water vapor molecules is $$v_{rel} := \sqrt{\frac{3 \cdot k_B \cdot T_r}{\left(\frac{M_{H2O}}{N_A}\right)}} = 637.353 \, \frac{m}{s}$$

Taking into account that only half of the molecules will fly toward the droplet surface we set $n=n_e/2$ and find $$Z := \frac{n_e}{2} \cdot A_d \cdot v_{rel} = 3.626 \times 10^{15} \, \frac{1}{s}$$

The evaporation rate ER of molecules from the water droplet is proportional to its surface $S=4A_d$ with a temperature-dependent proportionality constant $k_E(T)$: $ER=4*A_d*k(T)$. In thermodynamic equilibrium we have $Z=ER$, leading to this expression for $k_E(T)$:

$$k_E(T) := \frac{p_v(T)}{8} \cdot \sqrt{\frac{3 \cdot N_A}{M_{H2O} \cdot (k_B \cdot T)}}$$

Referring back to the example: At the initial temperature $T_r=20°$ C. the evaporation rate is $$ER := 4 \cdot A_d \cdot k_E(T_r) = 3.626 \times 10^{15} \, \frac{1}{s}$$

and the condensation rate (collision rate) is $$Z := \frac{n_r}{2} \cdot A_d \cdot v_{rel} = 2.303 \times 10^{15} \, \frac{1}{s}$$

The time constant for droplet evaporation is thus $$\tau_{ev} := \frac{N_{evap}}{ER - Z} = 0.118 \cdot ms$$

This time constant is indeed very small compared to the time scale of the breathing cycle—and also small compared to the time scale for diffusion/heat conduction. It is therefore meaningful to assume evaporation/condensation as "fast" (not rate-limiting) processes.

Regarding a time scale of water vapor diffusion and heat conduction, as stated, one can construct a 1D model with spherical symmetry which is covering the volume $V_{occ}$ occupied by one water droplet. The droplet radius is $R_d=D_d/2=2.5 \, \mu m$.

The radius $R_{occ}$ of the occupied volume is:

$$R_{occ} := \sqrt[3]{\frac{3}{4 \cdot \pi} \cdot V_{occ}} = 77.941 \cdot \mu m$$

The water vapor diffusion equation can be examined. The water vapor continuity equation and Fick's diffusion law are reading:

$$\frac{\partial}{\partial t} n + \nabla \cdot j_n = 0 \quad j_n = -D \cdot \nabla n$$

With $n$=water vapor density [1/m$^3$], $j_n$=water vapor flux density [1/m$^2$/s], D=water vapor diffusion coefficient ($2.62*10^{-5}$ m$^2$/s at 30° C., 1 atm). In spherical coordinates we have:

$$\frac{\partial}{\partial t} n - D \cdot \left[\frac{1}{R} \cdot \frac{\partial^2}{\partial R^2}(R \cdot n)\right] = 0$$

We assume a certain time dependence of n(t,R) to be able to separate the variables t and R (and to transform this PDE into an ODE):

$$n(t, R) = (n_f - n_s(R)) \cdot \left(1 - e^{\frac{-t}{\tau_d}}\right) + n_s(R)$$

$$\frac{d^2}{dR^2} n_s(R) + \frac{2}{R} \cdot \frac{d}{dR} n_s(R) - \frac{(n_f - n_s(R))}{\tau_d \cdot D} = 0$$

This means that n(t,R) will start with a certain distribution $n_s(R)$ and evolve into a homogeneous final distribution of with a "diffusion" time constant $\tau_d$. We thus obtain this ODE for the start distribution $n_s(R)$:

The two boundary conditions for integration are:

$$j_n(t, R_{occ}) = 0 \text{ (no loss of molecules from } V_{occ}) \Rightarrow \frac{d}{dR} n_s(R_{occ}) = 0$$

$n_s(R_{occ})=n_r$ (the start water vapor density at the edge of $V_{occ}$ is the initial air concentration $n_r$).

The diffusion time constant $\tau_d$ is yet unknown and will be determined later.

Examining the heat conduction equation, the energy balance equation is reading:

$$\frac{\partial}{\partial t} u + \nabla \cdot j_E = 0 \quad u = c_a \cdot C_{pa} \cdot T \quad j_E = -\lambda \cdot \nabla T$$

With u=energy density [J/m$^3$], $j_E$=energy flux density [W/m$^2$], $c_a$=air concentration [1.166 kg/m$^3$], $C_{pa}$=air heat capacity [1006 J/kg/K], $\lambda$=air thermal conductivity [0.026 W/m/K]. In spherical coordinates:

$$\frac{\partial}{\partial t} T - \alpha_a \cdot \left[\frac{1}{R} \cdot \frac{\partial^2}{\partial R^2}(R \cdot T)\right] = 0 \text{ with}$$

$$\alpha_a := \frac{\lambda(T_a)}{c_a \cdot C_{pa}(T_a)} = 2.218 \times 10^{-5} \frac{m^2}{s}$$

We assume again a certain time dependence of T(t,R):

$$T(t, R) = (T_f - T_s(R)) \cdot \left(1 - e^{\frac{-t}{\tau_E}}\right) + T_s(R)$$

The start temperature distribution $T_s(R)$ should fulfill this ODE:

$$\frac{d^2}{dR^2}T_s(R) + \frac{2}{R} \cdot \frac{d}{dR}T_s(R) - \frac{(T_f - T_s(R))}{\tau_E \cdot \alpha_s} = 0$$

The first boundary condition is: $T_s(R_d)$=TsL (the start temperature at the droplet surface is TsL).

The second boundary condition is derived from the integral energy balance of the droplet:

$$-m_d \cdot C_{pl} \cdot \left(\frac{\partial}{\partial t}T(t, R_d)\right) = 4 \cdot \pi \cdot R_d^2 \cdot \left(\frac{\Delta H}{N_A} \cdot j_n(t, R_d) + j_E(t, R_d)\right)$$

The left hand side term is the energy gain by cooling of the droplet [in W]. The first term on the right hand side is the energy loss by evaporation of water molecules and the second term on the RHS is the energy gain by heat conduction from the gas. Rearranging for $j_E$ we have:

$$j_E(t, R_d) = \frac{-m_d \cdot C_{pl}(T_a) \cdot \frac{\partial}{\partial t}T(t, R_d)}{4 \cdot \pi \cdot R_d^2} - \frac{\Delta H}{N_A} \cdot j_n(t, R_d)$$

This implies that the temperature dependence of $j_n(t,R_d) \propto \exp(-t/\tau_d)$ should be the same as the temperature dependence of $dT/dt$ and $j_E(t,R_d)$ (both $\propto \exp(-t/\tau_E)$). Therefore, we find $\tau_E = \tau_d$.

Evaluating the last equation at t=0 we find as second boundary condition:

$$\frac{d}{dR}T_s(R_d) = \frac{\Delta H}{N_A \cdot \lambda(T_a)} \cdot j_{ns}(R_d) + \frac{m_d \cdot C_{pl}(T_a) \cdot (T_f - TsL)}{4 \cdot \pi \cdot R_d^2 \cdot \lambda(T_a) \cdot \tau_d}$$

However, there are still two unknown parameters: $\tau_d$ and $TsL=T_s(R_d)$. These two parameters have to be iteratively adjusted until the last 2 boundary conditions are fulfilled:

$$n_s(R_d) = \frac{p_v(TsL)}{k_B \cdot TsL} \text{(thermodynamic equilibrium at the droplet surface)}$$

$$J_E(t, R_{occ}) = 0 \text{ ( = no loss of energy from } V_{occ}) \Rightarrow \frac{d}{dR}T_s(R_{occ}) = 0$$

In the example from above one obtains a consistent solution for $\tau_d$=2.525 ms and TsL=$T_s(R_d)$=15.31° C.

Note that TsL (the start temperature at the droplet radius) is slightly lower than the final, homogeneous temperature $T_f$=15.59° C. (Correspondingly, the start density at the droplet radius $n_s(Rd)$=4.39*10$^{23}$ 1/m$^3$ is slightly lower than the final, homogeneous density $n_f$=4.47*10$^{23}$ 1/m$^3$).

When comparing $T_d$=2.525 ms to the evaporation time $\tau_{ev}$=0.12 ms, it shows that the evaporation is "fast" compared to diffusion and conduction. Note that $T_s(R_{occ})$=20.52° C., i.e., 0.52° C. higher than the start temperature $T_r$=20° C. of the droplet plus room air ensemble. This is a consequence of energy conservation: If the droplet is cooling by 4.4° C. by "fast" evaporation, then the air has to warm up so that the total energy is staying constant.

The distance travelled during $2*\tau_d$ is examined. It is interesting to estimate the distance the air inhaled by the subject will have travelled until, say, 90% of the equilibrium between droplets and gas has been established. The total volume inhaled is $V_{inh}$=0.5 L. The duration of inhalation is $t_{inh}$=1 s. A typical tube diameter is 20 mm, corresponding to a tube cross section of $A_T$=3.14 cm$^2$. The average gas velocity in the tube during inhalation is thus $$v_{avinh} := \frac{V_{inh}}{A_T \cdot t_{inh}} = 1.592 \frac{m}{s}$$

90% of the equilibrium between droplets and gas has been established after $2*\tau_d$=5.05 ms. Finally, the average distance travelled by the mist in the tube during this time is $v_{avinh}*2*\tau_d$=0.80 cm.

This implies that the equilibrium between water droplets and surrounding gas will be already established before the mist comes into contact with the subject's tissue. It should be noted that the peak gas velocity on the axis during inhalation is $v_{pinh}$=(70 L/min)/(30 L/min)*2*$v_{avinh}$=7.43 m/s, i.e., a factor of 4.7 higher than $V_{avinh}$. The peak distance travelled on the axis until equilibrium is established is thus 0.80 cm*4.7=3.7 cm.

The transport phenomena in the occupied volume $V_{occ}$ for our "standard" conditions ($T_r$=20° C. and $c_l$=33 mg/L) is discussed herein. Further examples (questions) also considered include:

Which temperature should the supplied air have to (nearly) completely evaporate the injected droplets ($c_l$=33 mg/L)? What would the time until equilibrium $\tau_d$ be in this case?

Which temperature should the supplied air have, if one is aiming at a final equilibrium temperature of 25° C.? (This would be equivalent to a "conventional" humidifier supplying 100% RH at 25° C.). In this case we could also reduce the injected droplet concentration (e.g. to $c_l$=16 mg/L). What would the time until equilibrium $\tau_d$ be in this case?

Let us supply air and droplets at $T_r$=20° C. and $c_l$=16 mg/L and do a slow heating (without overshoot of temperature) after the injection of droplets so that the final equilibrium temperature is also 25° C. What would the time until equilibrium $\tau_d$ and the heating power be in this case?

The results of simulations are summarized in the following table:

| Parameter | $T_r$ = 20° C., $c_l$ = 33 mg/L | $T_f$ = 37° C., $c_l$ = 33 mg/L | $T_f$ = 25° C., $c_l$ = 16 mg/L | Slow heating |
|---|---|---|---|---|
| Start temperature $T_r$ | 20° C. | 95° C. | 48° C. | 20° C. |
| Start vapor conc. $c_r$ | 11 mg/L | 11 mg/L | 11 mg/L | 11 mg/L |
| Start rel. humidity | 63.5% | 2% | 14.4% | 63.5% |
| Start droplet conc. $c_l$ | 33 mg/L | 33 mg/L | 16 mg/L | 16 mg/L |
| Start droplet radius $R_d$ | 2.5 μm | 2.5 μm | 2.5 μm | 2.5 μm |
| Final temperature $T_f$ | 15.6° C. | 36.8° C. | 25.2° C. | 25.0° C. |
| Final vapor conc. $c_f$ | 13.4 mg/L | 43.6 mg/L | 23.4 mg/L | 23.0 mg/L |
| Evap. fraction of droplet | 7.1% | 98.7% | 77.2% | 75.2% |
| Final droplet radius $R_{df}$ | 2.44 μm | 0.60 μm | 1.53 μm | 1.57 μm |
| Time until equilib. $\tau_d$ | 2.525 ms | 2.30 ms | 5.18 ms | 30.0 ms |
| Heating energy density | — | — | — | 36 J/L |

The first example has already been discussed above.

The second example shows that the start temperature would have to be very high (95° C., probably yielding a safety issue), but the time needed to come into equilibrium is still very short (2.30 ms). It is shorter than in the first example, because the diffusion coefficient D is higher at the higher average temperature of 66° C. The average heating power during inhalation would be 49.2 W.

The third example appears quite attractive. When supplying air with a start temperature of 4° C. to a personal humidifier operating at half power ($c_i$=16 mg/L), then an equilibrium composition of 100% RH air at 25° C. with 3 μm diameter droplets is established with a time constant of 5.3 ms. This time constant is longer than in the first example, mainly because the diffusion length (radius $R_{occ}$ of the occupied volume) is increased when the number of droplets per volume is reduced. This time constant thus corresponds to an average travelled distance of 1.65 cm or a peak distance travelled on the axis of 7.75 cm. Such a "safety distance" between droplet injection and subject's tissue can be easily established. When combined with a fast thermocouple near the entrance of the tracheal cannula (to be able to switch off the air heating if the nebulizer stops injecting droplets) a safe device can be constructed. The average heating power during inhalation would be 18.4 W. An additional benefit is that the droplet size entering the tracheal cannula is diminished by evaporation (5 μm down to 3 μm) so that a larger fraction of droplets is able to reach the deeper airways without hitting the walls of the trach bend.

In the fourth example, it is assumed that the same situation as in the third example is desired ($T_f$=25° C.). As a consequence, an energy density of $e_h$=36 J/L is supplied to the air volume to realize this situation. The total inhaled volume is $V_{inh}$=0.5 L and the total time for inhalation is $t_{inh}$=1 s. The average heating power during inhalation is $P_h=e_h*V_{inh}/t_{inh}$=18 W. The peak heating power is 18 W*70 [L/min]/30[L/min]=42 W. The time dependence of the heating power density $p_h$ is assumed to be the same as for the diffusion/conduction terms, i.e., an exponential decrease with time constant $\tau_d$.

Unfortunately, the time constant $\tau_d$ is becoming very large (30 ms) in this example. This is a consequence of the fact that the temperature gradients (which are driving the conduction/diffusion phenomena) are now much smaller than in the third example. The average travelled distance until establishing the equilibrium is now 9.5 cm and the peak distance travelled on the axis is about 45 cm. These high distances until equilibrium let this proposition appear as rather impractical for a "personal humidifier." Of course one could apply a high power density. However, this would then necessarily lead to an overshoot in temperature, because a high temperature gradient close to the droplet surface is needed to come to the desired short time constant $\tau_d$.

Returning to FIG. 1, electronic storage 50 comprises electronic storage media that electronically stores information. The electronic storage media of electronic storage 50 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 50 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 50 may store software algorithms, information determined by processor 22, information received via user interface 20, and/or other information that enables system 10 to function properly. Electronic storage 50 may be (in whole or in part) a separate component within system 10, or electronic storage 50 may be provided (in whole or in part) integrally with one or more other components of system 10 (e.g., user interface 20, pressure generator 14, processor 22, etc.).

By way of a non-limiting example, electronic storage 50 may be configured to store information related to a comfort level of subject 12 and corresponding parameters of the pressurized flow of breathable gas. Electronic storage 50 may be configured to store information related to ambient weather conditions, a season of the year, and/or other information that corresponds to the comfort level of subject 12, parameters of the pressurized flow of breathable gas, and/or other information.

FIG. 8 illustrates a method 800 for adjusting humidity of a pressurized flow of breathable gas delivered to the airway of a subject with a pressure support system. The pressure support system comprises a pressure generator, a nebulizer, a heater, one or more sensors, a user interface, one or more physical computer processors, a subject interface, and/or other components. The operations of method 800 presented below are intended to be illustrative. In some embodiments, method 800 may be accomplished with one or more additional operations not described, and/or without one or more of the operations discussed. Additionally, the order in which the operations of method 800 are illustrated in FIG. 8 and described below is not intended to be limiting.

In some embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 800, a pressure generator generates a pressurized flow of breathable gas for delivery to an airway of subject 12. In some embodiments, operation 800 is performed by a pressure generator the same as or similar to pressure generator 14 (shown in FIG. 1 and described herein).

At an operation 804, the pressurized flow of breathable gas is humidified (i.e., moisture is provided to the pressurized flow of breathable gas). In some embodiments, operation 804 is performed by a nebulizer the same as or similar to nebulizer 16 (shown in FIG. 1 and described herein).

At an operation 806, a volume of the breathable gas is heated before fluid droplets are provided to the breathable gas (i.e., before operation 804). In some embodiments, operation 906 is performed by a heater the same as or similar to one or more sensors the same as or similar to heater 38 (shown in FIGS. 1 and 4 and described herein). The breathable gas received by subject 12 exhibits a target temperature and humidity level at short distance d (mentioned herein) from the nebulizer due to one or more of a number of the droplets, an average size of the droplets, a gas flow rate, and/or an amount of heating power.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to facilitate humidification of a pressurized flow of breathable gas delivered to a subject, the system comprising:
    a pressure generator configured to generate a pressurized flow of breathable gas for delivery to an airway within a trachea of the subject;
    a nebulizer configured to provide a mist of fluid droplets to the breathable gas;
    a heater configured to heat a volume of the breathable gas before the mist of fluid droplets are supplied to the breathable gas;
    one or more hardware processors configured by machine-readable instructions to:
        cause the pressure generator to deliver a flow of breathable gas to the subject;
        cause the nebulizer to provide the mist of fluid droplets to the breathable gas; and
        cause the heater to heat a volume of the breathable gas before the mist of fluid droplets are supplied to the breathable gas; and
    a tracheal cannula being communicatively coupled with the pressure generator;
    wherein a gas flow rate, a fluid droplet size of the mist of fluid droplets, an inner lumen diameter of the tracheal cannula, and a curvature radius of the tracheal cannula are tuned to facilitate delivery of the mist of fluid droplets to the trachea of the subject to reduce impaction; and
    wherein the breathable gas received by the subject exhibits a target temperature and humidity level at short distance d from the nebulizer due to one or more of a number of fluid droplets of the mist of fluid droplets, an average size of the fluid droplets, the gas flow rate, and/or an amount of heating power, wherein the distance d is in a range from 1 cm to 30 cm.

2. The system of claim 1, further comprising a temperature sensor located at an entrance leading to the subject to facilitate controlling operating conditions.

3. The system of claim 2, wherein the temperature sensor is configured to trigger a switch-off of the heater when a threshold temperature is reached at the entrance leading to the subject indicating that the nebulizer is failing to produce the mist of fluid droplets.

4. The system of claim 1, wherein the inner lumen diameter and the curvature radius facilitate the delivery of the mist of fluid droplets to the trachea of the subject such that the breathable gas received by the subject exhibits the target temperature and humidity level, wherein the fluid droplets are fully evaporated.

5. The system of claim 1, wherein the inner lumen diameter falls within a range of about 4 mm to about 11 mm.

6. The system of claim 1, wherein the curvature radius falls within a range of about 17 mm to about 25 mm.

7. The system of claim 1, wherein a time-dependent air heating power is modulated and proportional to the flow of breathable gas, wherein there is no heating during exhalation.

8. The system of claim 1, wherein a target temperature of between about room temperature and 42° C. and a relative humidity are maintained at an interface to the subject, the relative humidity being about 100%.

9. The system of claim 1, wherein the gas flow rate, the fluid droplet size of the mist of fluid droplets, the inner lumen diameter of the tracheal cannula, and the curvature radius of the tracheal cannula are tuned to not exceed a threshold impaction criterion.

10. A method for facilitating humidification of a pressurized flow of gas delivered by a system comprising a pressure generator, a nebulizer, a heater, and one or more hardware processors, the method comprising:
    generating, with the pressure generator, a pressurized flow of gas;
    providing a mist of fluid droplets, with the nebulizer, to the pressurized flow of gas; and
    heating, with the heater, a volume of the gas before the mist of fluid droplets are supplied to the gas; and
    tuning a gas flow rate, a fluid droplet size of the mist of fluid droplets, an inner lumen diameter of a tracheal cannula, and a curvature radius of the tracheal cannula to facilitate delivery of the mist of fluid droplets to the trachea of a subject to reduce impaction;
    wherein the gas delivered by the system exhibits a target temperature and humidity level at short distance d from the nebulizer due to one or more of a number of fluid droplets of the mist of fluid droplets, an average size of the fluid droplets, the gas flow rate, and/or an amount of heating power, wherein the distance d is in a range from 1 cm to 30 cm.

11. The method of claim 10, the one or more hardware processors are further configured to use a temperature sensor to trigger a switch-off of the heater when a threshold temperature is reached at an interface of the system, indicating that the nebulizer is failing to produce the mist of fluid droplets.

12. The method of claim 10, wherein the inner lumen diameter and the curvature radius facilitate the delivery of the mist of fluid droplets such that the delivered gas exhibits the target temperature and humidity level, wherein the fluid droplets are fully evaporated.

13. The method of claim 12, wherein the inner lumen diameter falls within a range of about 4 mm to about 11 mm.

14. The method of claim 12, wherein the curvature radius falls within a range of about 17 mm to about 25 mm.

15. A system for facilitating humidification of a pressurized flow of breathable gas delivered to a subject, the system comprising:
    means for generating a pressurized flow of breathable gas for delivery to an airway within a trachea of the subject;
    means for providing a mist of fluid droplets to the pressurized flow of breathable gas; and
    means for heating a volume of the breathable gas before the mist of fluid droplets are supplied to the breathable gas; and a tracheal cannula means being communicatively coupled with the means for generating a pressurized flow;

wherein a gas flow rate, a fluid droplet size of the mist of fluid droplets, an inner lumen diameter of the tracheal cannula means, and a curvature radius of the tracheal cannula means are tuned to facilitate delivery of the mist of fluid droplets to the trachea of the subject to reduce impaction; and wherein the breathable gas received by the subject exhibits a target temperature and humidity level at short distance d from the means for providing a mist of fluid droplets due to one or more of a number of fluid droplets of the mist of fluid droplets, an average size of the fluid droplets, a gas flow rate, and/or an amount of heating power, wherein the distance d is in a range from 1 cm to 30 cm.

16. The system of claim 15, wherein the means for providing fluid droplets is a vibrating mesh nebulizer configured to cause a mist of water droplets of a defined diameter to be generated.

17. The system of claim 15, further comprising a means for facilitating controlling operating conditions, the means for facilitating controlling operating conditions located at an entrance of the means for facilitating the delivery of fluid droplets to the trachea of the subject.

18. The system of claim 15, wherein the means for facilitating controlling operating conditions is configured to a switch-off of the means for heating if the means for providing a mist of fluid droplets to the pressurized flow of breathable gas fails to produce the mist of fluid droplets.

\* \* \* \* \*